US 10,603,105 B2

(12) United States Patent
Cheung et al.

(10) Patent No.: US 10,603,105 B2
(45) Date of Patent: Mar. 31, 2020

(54) MEDICAL DEVICES WITH A FLEXIBLE ELECTRODE ASSEMBLY COUPLED TO AN ABLATION TIP

(71) Applicant: Boston Scientific Scimed Inc., Maple Grove, MN (US)

(72) Inventors: Desmond Cheung, San Jose, CA (US); John C. Potosky, San Jose, CA (US); Andrew T. Marecki, Shrewsbury, MA (US); Isaac J. Kim, San Jose, CA (US); Mark D. Mirigian, San Jose, CA (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 759 days.

(21) Appl. No.: 14/922,023

(22) Filed: Oct. 23, 2015

(65) Prior Publication Data
US 2016/0113712 A1    Apr. 28, 2016

Related U.S. Application Data

(60) Provisional application No. 62/068,334, filed on Oct. 24, 2014.

(51) Int. Cl.
*A61B 18/14*     (2006.01)
*A61B 5/00*      (2006.01)
(Continued)

(52) U.S. Cl.
CPC ........ *A61B 18/1492* (2013.01); *A61B 5/0422* (2013.01); *A61B 5/6852* (2013.01);
(Continued)

(58) Field of Classification Search
CPC ................ A61B 2018/1465; A61B 2018/1495
See application file for complete search history.

(56) References Cited

U.S. PATENT DOCUMENTS 3,773,401 A    11/1973  Douklias et al.
4,466,443 A     8/1984  Utsugi
(Continued)

FOREIGN PATENT DOCUMENTS

CA    2682055 A1   10/2008
CA    2847846 A1    3/2013
(Continued)

OTHER PUBLICATIONS

International Preliminary Report on Patentability issued in PCT/US2015/021300 dated Sep. 29, 2016, 7 pages.
(Continued)

*Primary Examiner* — Michael F Peffley
*Assistant Examiner* — Bo Ouyang
(74) *Attorney, Agent, or Firm* — Faegre Drinker Biddle & Reath LLP

(57) ABSTRACT

Medical devices and methods for making and using medical devices are disclosed. An example medical device may include a catheter for use in cardiac mapping and/or ablation. The catheter may include an elongate catheter shaft having a distal ablation electrode region capable of ablating tissue. An electrode assembly may be coupled to the distal ablation electrode region. The electrode assembly may include a flexible circuit having one or more electrodes disposed thereon.

20 Claims, 37 Drawing Sheets

(51) Int. Cl.
*A61B 5/042* (2006.01)
*A61B 18/00* (2006.01)
*A61B 17/00* (2006.01)

(52) U.S. Cl.
CPC .. *A61B 5/6859* (2013.01); *A61B 2017/00526* (2013.01); *A61B 2018/00351* (2013.01); *A61B 2018/00577* (2013.01); *A61B 2018/00642* (2013.01); *A61B 2018/00839* (2013.01); *A61B 2018/1465* (2013.01); *A61B 2018/1495* (2013.01); *A61B 2562/166* (2013.01)

(56) References Cited

U.S. PATENT DOCUMENTS

| | | |
|---|---|---|
| 4,602,624 A | 7/1986 | Naples et al. |
| 4,633,882 A | 1/1987 | Matsuo et al. |
| 4,732,149 A | 3/1988 | Sutter |
| 4,745,928 A | 5/1988 | Webler et al. |
| 4,763,660 A | 8/1988 | Kroll et al. |
| 4,966,145 A | 10/1990 | Kikumoto et al. |
| 5,019,076 A | 5/1991 | Yamanashi et al. |
| 5,029,588 A | 7/1991 | Yock et al. |
| 5,114,423 A | 5/1992 | Kasprzyk et al. |
| 5,178,150 A | 1/1993 | Silverstein et al. |
| 5,217,460 A | 6/1993 | Knoepfler |
| 5,238,004 A | 8/1993 | Sahatjian et al. |
| 5,240,003 A | 8/1993 | Lancee et al. |
| 5,242,441 A | 9/1993 | Avitall |
| 5,254,088 A | 10/1993 | Lundquist et al. |
| 5,277,201 A | 1/1994 | Stern |
| 5,295,482 A | 3/1994 | Clare et al. |
| 5,318,589 A | 6/1994 | Lichtman |
| 5,324,284 A | 6/1994 | Imran |
| 5,331,966 A | 7/1994 | Bennett et al. |
| 5,334,193 A | 8/1994 | Nardella |
| 5,341,807 A | 8/1994 | Nardella |
| 5,377,685 A | 1/1995 | Kazi et al. |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,415,654 A | 5/1995 | Daikuzono |
| 5,417,689 A | 5/1995 | Fine |
| 5,423,811 A | 6/1995 | Imran et al. |
| 5,447,529 A | 9/1995 | Marchlinski et al. |
| 5,456,682 A | 10/1995 | Edwards et al. |
| 5,462,521 A | 10/1995 | Brucker et al. |
| 5,482,054 A | 1/1996 | Slater et al. |
| 5,485,849 A | 1/1996 | Panescu et al. |
| 5,494,042 A | 2/1996 | Panescu et al. |
| 5,500,012 A | 3/1996 | Brucker et al. |
| 5,520,683 A | 5/1996 | Subramaniam et al. |
| 5,571,088 A | 11/1996 | Lennox et al. |
| 5,573,535 A | 11/1996 | Viklund |
| 5,575,772 A | 11/1996 | Lennox |
| 5,579,764 A | 12/1996 | Goldreyer |
| 5,582,609 A | 12/1996 | Swanson et al. |
| 5,647,870 A | 7/1997 | Kordis et al. |
| 5,718,701 A | 2/1998 | Shai et al. |
| 5,722,402 A | 3/1998 | Swanson et al. |
| 5,735,846 A | 4/1998 | Panescu et al. |
| 5,762,067 A | 6/1998 | Dunham et al. |
| 5,788,636 A | 8/1998 | Curley |
| 5,792,064 A | 8/1998 | Panescu et al. |
| 5,800,482 A | 9/1998 | Pomeranz et al. |
| 5,820,568 A | 10/1998 | Willis |
| 5,830,213 A | 11/1998 | Panescu et al. |
| 5,833,621 A | 11/1998 | Panescu et al. |
| 5,836,990 A | 11/1998 | Li |
| 5,868,735 A | 2/1999 | Lafontaine |
| 5,871,483 A | 2/1999 | Jackson et al. |
| 5,871,526 A | 2/1999 | Gibbs et al. |
| 5,876,336 A | 3/1999 | Swanson et al. |
| 5,885,278 A | 3/1999 | Fleischman |
| 5,913,856 A | 6/1999 | Chia et al. |
| 5,916,213 A | 6/1999 | Haissaguerre et al. |
| 5,957,850 A | 9/1999 | Marian et al. |
| 6,004,269 A | 12/1999 | Crowley et al. |
| 6,027,500 A | 2/2000 | Buckles et al. |
| 6,050,267 A | 4/2000 | Nardella et al. |
| 6,050,994 A | 4/2000 | Sherman |
| 6,059,778 A | 5/2000 | Sherman |
| 6,063,078 A | 5/2000 | Wittkampf |
| 6,064,905 A | 5/2000 | Webster, Jr. et al. |
| 6,068,629 A | 5/2000 | Haissaguerre et al. |
| 6,070,094 A | 5/2000 | Swanson et al. |
| 6,071,281 A * | 6/2000 | Burnside ............ A61B 18/1482 606/37 |
| 6,083,170 A | 7/2000 | Ben-Haim |
| 6,083,222 A | 7/2000 | Klein et al. |
| 6,099,524 A | 8/2000 | Lipson et al. |
| 6,101,409 A | 8/2000 | Swanson et al. |
| 6,116,027 A | 9/2000 | Smith et al. |
| 6,120,476 A | 9/2000 | Fung et al. |
| 6,165,123 A | 12/2000 | Thompson |
| 6,171,305 B1 | 1/2001 | Sherman |
| 6,200,314 B1 | 3/2001 | Sherman |
| 6,206,831 B1 | 3/2001 | Suorsa et al. |
| 6,210,337 B1 | 4/2001 | Dunham et al. |
| 6,216,027 B1 | 4/2001 | Willis et al. |
| 6,224,557 B1 | 5/2001 | Ziel et al. |
| 6,233,491 B1 | 5/2001 | Kordis et al. |
| 6,241,754 B1 | 6/2001 | Swanson et al. |
| 6,270,493 B1 | 8/2001 | Lalonde et al. |
| 6,290,697 B1 | 9/2001 | Tu et al. |
| 6,352,534 B1 | 3/2002 | Paddock et al. |
| 6,395,325 B1 | 5/2002 | Hedge et al. |
| 6,400,981 B1 | 6/2002 | Govari |
| 6,423,002 B1 | 7/2002 | Hossack |
| 6,475,213 B1 | 11/2002 | Whayne et al. |
| 6,488,678 B2 | 12/2002 | Sherman |
| 6,491,710 B2 | 12/2002 | Satake |
| 6,500,174 B1 | 12/2002 | Maguire et al. |
| 6,508,767 B2 | 1/2003 | Burns et al. |
| 6,508,769 B2 | 1/2003 | Bonnefous |
| 6,508,803 B1 | 1/2003 | Horikawa et al. |
| 6,514,249 B1 | 2/2003 | Maguire et al. |
| 6,516,667 B1 | 2/2003 | Broad et al. |
| 6,517,533 B1 | 2/2003 | Swaminathan |
| 6,517,534 B1 | 2/2003 | McGovern et al. |
| 6,537,271 B1 | 3/2003 | Murray et al. |
| 6,544,175 B1 | 4/2003 | Newman |
| 6,546,270 B1 | 4/2003 | Goldin et al. |
| 6,547,788 B1 | 4/2003 | Maguire et al. |
| 6,569,160 B1 | 5/2003 | Goldin et al. |
| 6,572,547 B2 | 6/2003 | Miller et al. |
| 6,575,966 B2 | 6/2003 | Lane et al. |
| 6,575,969 B1 | 6/2003 | Rittman et al. |
| 6,579,278 B1 | 6/2003 | Bencini |
| 6,582,372 B2 | 6/2003 | Poland |
| 6,584,345 B2 | 6/2003 | Govari |
| 6,589,182 B1 | 7/2003 | Loftman et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,647,281 B2 | 11/2003 | Morency |
| 6,656,174 B1 | 12/2003 | Hegde et al. |
| 6,658,279 B2 | 12/2003 | Swanson et al. |
| 6,663,573 B2 | 12/2003 | Goldin |
| 6,666,862 B2 | 12/2003 | Jain et al. |
| 6,673,067 B1 | 1/2004 | Peyman |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,719,756 B1 | 4/2004 | Muntermann |
| 6,723,094 B1 | 4/2004 | Desinger |
| 6,735,465 B2 | 5/2004 | Panescu |
| 6,736,814 B2 | 5/2004 | Manna et al. |

(56) References Cited

U.S. PATENT DOCUMENTS

| | | |
|---|---|---|
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,804,545 B2 | 10/2004 | Fuimaono et al. |
| 6,811,550 B2 | 11/2004 | Holland et al. |
| 6,824,517 B2 | 11/2004 | Salgo et al. |
| 6,837,884 B2 | 1/2005 | Woloszko |
| 6,845,257 B2 | 1/2005 | Fuimaono et al. |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,923,808 B2 | 8/2005 | Taimisto |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,099,711 B2 | 8/2006 | Fuimaono et al. |
| 7,105,122 B2 | 9/2006 | Karason |
| 7,112,198 B2 | 9/2006 | Satake |
| 7,115,122 B1 | 10/2006 | Swanson et al. |
| 7,123,951 B2 | 10/2006 | Fuimaono et al. |
| 7,131,947 B2 | 11/2006 | Demers |
| 7,166,075 B2 | 1/2007 | Varghese et al. |
| 7,181,262 B2 | 2/2007 | Fuimaono et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D'Sa |
| 7,347,820 B2 | 3/2008 | Bonnefous |
| 7,347,821 B2 | 3/2008 | Dkyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,610,073 B2 | 10/2009 | Fuimaono et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,879,029 B2 | 2/2011 | Jimenez |
| 7,892,228 B2 | 2/2011 | Landis et al. |
| 7,894,871 B2 | 2/2011 | Wittkampf et al. |
| 7,918,850 B2 | 4/2011 | Govari et al. |
| 7,957,817 B1 | 6/2011 | Gillespie et al. |
| 7,996,085 B2 | 8/2011 | Levin |
| 8,016,822 B2 | 9/2011 | Swanson |
| 8,048,028 B2 | 11/2011 | Horn et al. |
| 8,103,327 B2 | 1/2012 | Harlev et al. |
| 8,128,617 B2 | 3/2012 | Bencini et al. |
| 8,160,690 B2 | 4/2012 | Wilfley et al. |
| 8,162,935 B2 | 4/2012 | Paul et al. |
| 8,265,745 B2 | 9/2012 | Hauck et al. |
| 8,267,926 B2 | 9/2012 | Paul et al. |
| 8,290,578 B2 | 10/2012 | Schneider |
| 8,317,783 B2 | 11/2012 | Cao et al. |
| 8,369,922 B2 | 2/2013 | Paul |
| 8,400,164 B2 | 3/2013 | Osadchy et al. |
| 8,403,925 B2 | 3/2013 | Miller et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,454,538 B2 | 6/2013 | Wittkampf et al. |
| 8,454,589 B2 | 6/2013 | Deno et al. |
| 8,489,184 B2 | 7/2013 | Wilfley et al. |
| 8,579,889 B2 | 11/2013 | Bencini |
| 8,583,215 B2 | 11/2013 | Lichtenstein |
| 8,603,084 B2 | 12/2013 | Fish et al. |
| 8,603,085 B2 | 12/2013 | Jimenez |
| 8,644,950 B2 | 2/2014 | Hauck |
| 8,657,814 B2 | 2/2014 | Werneth et al. |
| 8,672,936 B2 | 3/2014 | Thao et al. |
| 8,679,109 B2 | 3/2014 | Paul et al. |
| 8,728,077 B2 | 5/2014 | Paul et al. |
| 8,740,900 B2 | 6/2014 | Kim et al. |
| 8,755,860 B2 | 6/2014 | Paul et al. |
| 8,771,343 B2 | 7/2014 | Weber et al. |
| 8,876,817 B2 | 11/2014 | Avitall et al. |
| 8,894,643 B2 | 11/2014 | Watson et al. |
| 8,906,011 B2 | 12/2014 | Gelbart et al. |
| 8,945,015 B2 | 2/2015 | Rankin et al. |
| 8,998,890 B2 | 4/2015 | Paul et al. |
| 9,089,340 B2 | 7/2015 | Hastings et al. |
| 9,125,565 B2 | 9/2015 | Hauck |
| 9,125,668 B2 | 9/2015 | Subramaniam et al. |
| 9,168,004 B2 | 10/2015 | Gliner et al. |
| 9,173,586 B2 | 11/2015 | Deno et al. |
| 9,211,156 B2 | 12/2015 | Kim et al. |
| 9,241,687 B2 | 1/2016 | McGee |
| 9,241,761 B2 | 1/2016 | Rankin et al. |
| 9,254,163 B2 | 2/2016 | Paul et al. |
| 9,265,434 B2 | 2/2016 | Merschon et al. |
| 9,271,782 B2 | 3/2016 | Paul et al. |
| 9,283,026 B2 | 3/2016 | Paul et al. |
| 9,370,329 B2 | 6/2016 | Tun et al. |
| 9,393,072 B2 | 7/2016 | Kim et al. |
| 9,463,064 B2 | 10/2016 | Subramaniam et al. |
| 9,603,659 B2 | 3/2017 | Subramaniam et al. |
| 9,757,191 B2 | 9/2017 | Avitall et al. |
| 2001/0029371 A1 | 10/2001 | Kordis |
| 2001/0034518 A1 | 10/2001 | Edwards et al. |
| 2002/0007180 A1 | 1/2002 | Wittenberger et al. |
| 2002/0087208 A1 | 7/2002 | Koblish et al. |
| 2002/0165448 A1 | 11/2002 | Ben-Haim et al. |
| 2002/0183735 A1 | 12/2002 | Edwards et al. |
| 2002/0198521 A1 | 12/2002 | Maguire |
| 2003/0004505 A1 | 1/2003 | Bencini et al. |
| 2003/0004506 A1 | 1/2003 | Messing |
| 2003/0013958 A1 | 1/2003 | Govari et al. |
| 2003/0014095 A1 | 1/2003 | Kramer et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0006268 A1 | 1/2004 | Gilboa et al. |
| 2004/0082860 A1 | 4/2004 | Haissaguerre |

(56) References Cited

U.S. PATENT DOCUMENTS

| | | |
|---|---|---|
| 2004/0092806 A1 | 5/2004 | Sagon et al. |
| 2004/0116793 A1 | 6/2004 | Taimisto et al. |
| 2004/0147920 A1 | 7/2004 | Keidar |
| 2004/0158238 A1 | 8/2004 | Lalonde et al. |
| 2004/0162556 A1 | 8/2004 | Swanson |
| 2004/0186467 A1 | 9/2004 | Swanson et al. |
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0165391 A1 | 7/2005 | Maguire et al. |
| 2005/0187544 A1 | 8/2005 | Swanson et al. |
| 2005/0203597 A1 | 9/2005 | Yamazaki et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2005/0288667 A1 | 12/2005 | Thompson et al. |
| 2006/0030919 A1 | 2/2006 | Mrva et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0224153 A1 | 10/2006 | Fischell et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0049925 A1 | 3/2007 | Phan et al. |
| 2007/0055225 A1 | 3/2007 | Dodd, III et al. |
| 2007/0073135 A1 | 3/2007 | Lee et al. |
| 2007/0088345 A1 | 4/2007 | Larson et al. |
| 2007/0165916 A1 | 7/2007 | Cloutier et al. |
| 2007/0167813 A1 | 7/2007 | Lee et al. |
| 2007/0181139 A1 | 8/2007 | Hauck |
| 2007/0225610 A1 | 9/2007 | Mickley et al. |
| 2007/0238997 A1 | 10/2007 | Camus |
| 2007/0270794 A1 | 11/2007 | Anderson et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0051841 A1 | 2/2008 | Swerdlow et al. |
| 2008/0058836 A1 | 3/2008 | Moll et al. |
| 2008/0086073 A1 | 4/2008 | McDaniel |
| 2008/0091109 A1 | 4/2008 | Abraham |
| 2008/0140065 A1 | 6/2008 | Rioux et al. |
| 2008/0161705 A1 | 7/2008 | Podmore et al. |
| 2008/0161795 A1 | 7/2008 | Wang et al. |
| 2008/0161796 A1 | 7/2008 | Cao et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2008/0300454 A1 | 12/2008 | Goto |
| 2008/0312521 A1 | 12/2008 | Solomon |
| 2008/0312713 A1 | 12/2008 | Wilfley et al. |
| 2009/0005771 A1 | 1/2009 | Lieber et al. |
| 2009/0030312 A1 | 1/2009 | Hadjicostis |
| 2009/0048591 A1 | 2/2009 | Ibrahim et al. |
| 2009/0056344 A1 | 3/2009 | Poch |
| 2009/0062790 A1 | 3/2009 | Malchano et al. |
| 2009/0062795 A1 | 3/2009 | Vakharia et al. |
| 2009/0076390 A1 | 3/2009 | Lee et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |
| 2009/0131932 A1 | 5/2009 | Vakharia et al. |
| 2009/0163904 A1 | 6/2009 | Miller et al. |
| 2009/0171341 A1 | 7/2009 | Pope et al. |
| 2009/0171345 A1 | 7/2009 | Miller et al. |
| 2009/0177069 A1 | 7/2009 | Razavi |
| 2009/0177111 A1 | 7/2009 | Miller et al. |
| 2009/0182316 A1 | 7/2009 | Bencini |
| 2009/0209950 A1 | 8/2009 | Starksen |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0275827 A1 | 11/2009 | Aiken et al. |
| 2009/0281541 A1 | 11/2009 | Ibrahim et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2009/0306643 A1 | 12/2009 | Pappone et al. |
| 2010/0010487 A1 | 1/2010 | Phan et al. |
| 2010/0030204 A1 | 2/2010 | Stein et al. |
| 2010/0057072 A1 | 3/2010 | Roman et al. |
| 2010/0076402 A1 | 3/2010 | Mazzone et al. |
| 2010/0076426 A1* | 3/2010 | de la Rama ....... A61B 18/1492 606/41 |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0114092 A1 | 5/2010 | Eisele et al. |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168570 A1 | 7/2010 | Sliwa et al. |
| 2010/0168831 A1 | 7/2010 | Korivi et al. |
| 2010/0241117 A1 | 9/2010 | Paul et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0268217 A1* | 10/2010 | Habib ................ A61B 17/2202 606/33 |
| 2010/0298826 A1 | 11/2010 | Leo et al. |
| 2010/0331658 A1 | 12/2010 | Kim et al. |
| 2011/0028820 A1 | 2/2011 | Lau et al. |
| 2011/0034915 A1 | 2/2011 | Ibrahim et al. |
| 2011/0071400 A1 | 3/2011 | Hastings et al. |
| 2011/0071401 A1 | 3/2011 | Hastings et al. |
| 2011/0112569 A1 | 5/2011 | Friedman et al. |
| 2011/0125143 A1 | 5/2011 | Gross et al. |
| 2011/0130648 A1 | 6/2011 | Beeckler et al. |
| 2011/0137153 A1 | 6/2011 | Govari et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2011/0237933 A1 | 9/2011 | Cohen |
| 2011/0282249 A1 | 11/2011 | Tsoref et al. |
| 2011/0319782 A1 | 12/2011 | Sweeney et al. |
| 2012/0004547 A1 | 1/2012 | Harks et al. |
| 2012/0029504 A1 | 2/2012 | Afonso et al. |
| 2012/0071870 A1* | 3/2012 | Salahieh ................ A61B 5/01 606/33 |
| 2012/0095347 A1 | 4/2012 | Adam et al. |
| 2012/0101398 A1 | 4/2012 | Ramanathan et al. |
| 2012/0116537 A1 | 5/2012 | Liebetanz |
| 2012/0136346 A1 | 5/2012 | Condie et al. |
| 2012/0136348 A1 | 5/2012 | Condie et al. |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0172871 A1 | 7/2012 | Hastings et al. |

(56) References Cited

U.S. PATENT DOCUMENTS

| | | |
|---|---|---|
| 2012/0238897 A1 | 9/2012 | Wilfley et al. |
| 2012/0310064 A1 | 12/2012 | McGee |
| 2012/0330304 A1 | 12/2012 | Vegesna et al. |
| 2013/0023784 A1 | 1/2013 | Schneider et al. |
| 2013/0023897 A1 | 1/2013 | Wallace |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079763 A1 | 3/2013 | Heckel et al. |
| 2013/0165926 A1 | 6/2013 | Mathur et al. |
| 2013/0172715 A1 | 7/2013 | Just et al. |
| 2013/0172742 A1 | 7/2013 | Rankin et al. |
| 2013/0172875 A1 | 7/2013 | Govari et al. |
| 2013/0184706 A1 | 7/2013 | Gelbart et al. |
| 2013/0190747 A1 | 7/2013 | Koblish et al. |
| 2013/0197363 A1 | 8/2013 | Rankin et al. |
| 2013/0226169 A1 | 8/2013 | Miller et al. |
| 2013/0274582 A1 | 10/2013 | Afonso et al. |
| 2013/0331739 A1 | 12/2013 | Gertner |
| 2013/0345537 A1 | 12/2013 | Thakur et al. |
| 2014/0012251 A1 | 1/2014 | Himmelstein et al. |
| 2014/0058375 A1 | 2/2014 | Koblish |
| 2014/0066764 A1 | 3/2014 | Subramaniam et al. |
| 2014/0073893 A1 | 3/2014 | Bencini |
| 2014/0075753 A1 | 3/2014 | Haarer et al. |
| 2014/0081111 A1 | 3/2014 | Tun et al. |
| 2014/0081112 A1 | 3/2014 | Kim et al. |
| 2014/0081113 A1 | 3/2014 | Cohen et al. |
| 2014/0081262 A1 | 3/2014 | Koblish et al. |
| 2014/0100563 A1 | 4/2014 | Govari et al. |
| 2014/0107453 A1 | 4/2014 | Maskara et al. |
| 2014/0107636 A1 | 4/2014 | Bencini |
| 2014/0128757 A1 | 5/2014 | Banet et al. |
| 2014/0142393 A1* | 5/2014 | Piskun .................. A61M 39/22 600/206 |
| 2014/0194867 A1 | 7/2014 | Fish et al. |
| 2014/0200429 A1 | 7/2014 | Spector et al. |
| 2014/0200430 A1 | 7/2014 | Spector |
| 2014/0214028 A1 | 7/2014 | Gelbart et al. |
| 2014/0228713 A1 | 8/2014 | Thao et al. |
| 2014/0243917 A1 | 8/2014 | Morley et al. |
| 2014/0261985 A1 | 9/2014 | Selkee |
| 2014/0275916 A1 | 9/2014 | Nabutovsky et al. |
| 2014/0276052 A1 | 9/2014 | Rankin et al. |
| 2014/0276811 A1 | 9/2014 | Koblish et al. |
| 2014/0330150 A1 | 11/2014 | Thakur et al. |
| 2014/0336518 A1 | 11/2014 | Shuros et al. |
| 2014/0358137 A1 | 12/2014 | Hu |
| 2014/0364715 A1 | 12/2014 | Hauck |
| 2014/0364843 A1 | 12/2014 | Paul et al. |
| 2014/0364848 A1 | 12/2014 | Heimbecher et al. |
| 2015/0005624 A1 | 1/2015 | Hauck et al. |
| 2015/0011995 A1 | 1/2015 | Avitall et al. |
| 2015/0018813 A1 | 1/2015 | Gliner |
| 2015/0133914 A1 | 5/2015 | Koblish |
| 2015/0133920 A1 | 5/2015 | Rankin et al. |
| 2015/0265341 A1 | 9/2015 | Koblish |
| 2015/0265348 A1 | 9/2015 | Avitall et al. |
| 2015/0342672 A1 | 12/2015 | Bencini et al. |
| 2015/0374252 A1 | 12/2015 | de la Rama et al. |
| 2015/0374436 A1 | 12/2015 | Subramaniam et al. |
| 2016/0008065 A1 | 1/2016 | Gliner et al. |
| 2016/0100884 A1 | 4/2016 | Fay et al. |

FOREIGN PATENT DOCUMENTS

| | | |
|---|---|---|
| CA | 2848053 A1 | 3/2013 |
| CN | 1269708 A | 10/2000 |
| CN | 1455655 A | 11/2003 |
| CN | 1674836 A | 9/2005 |
| CN | 1942145 A | 4/2007 |
| CN | 102271607 A | 12/2011 |
| CN | 102573966 A | 7/2012 |
| CN | 103917185 A | 7/2014 |
| CN | 103987336 A | 8/2014 |
| CN | 104039257 A | 9/2014 |
| CN | 104244810 A | 12/2014 |
| CN | 104254368 A | 12/2014 |
| CN | 104619259 A | 5/2015 |
| CN | 104640513 A | 5/2015 |
| CN | 104661609 A | 5/2015 |
| EP | 1343426 B1 | 9/2003 |
| EP | 1343427 B1 | 9/2003 |
| EP | 1502542 A1 | 2/2005 |
| EP | 1547537 A1 | 6/2005 |
| EP | 0985423 B1 | 4/2006 |
| EP | 1717601 A2 | 11/2006 |
| EP | 1935332 A2 | 6/2008 |
| EP | 2755587 A | 7/2014 |
| EP | 2755588 A | 7/2014 |
| EP | 2136702 B1 | 7/2015 |
| EP | 2897545 A1 | 7/2015 |
| JP | H07100214 A | 4/1995 |
| JP | 2000000242 A | 1/2000 |
| JP | 200083918 A | 3/2000 |
| JP | 2000504242 A | 4/2000 |
| JP | 2002528039 A | 8/2002 |
| JP | 2003504090 A | 2/2003 |
| JP | 2004503335 A | 2/2004 |
| JP | 2006239414 A | 9/2006 |
| JP | 2007163559 A | 6/2007 |
| JP | 2007244857 A | 9/2007 |
| JP | 2009142653 A | 12/2008 |
| JP | 2009518150 A | 5/2009 |
| JP | 2010522623 A | 7/2010 |
| JP | 2011142995 A | 7/2011 |
| JP | 2011525842 A | 9/2011 |
| JP | 2012531967 A | 12/2012 |
| JP | 5336465 B2 | 11/2013 |
| JP | 2014012174 A | 1/2014 |
| JP | 2014531244 A | 11/2014 |
| JP | 2015501162 A | 1/2015 |
| JP | 2015509027 A | 3/2015 |
| KR | 20100021401 A | 2/2010 |
| KR | 101490374 B1 | 2/2015 |
| WO | WO199221278 A1 | 12/1992 |
| WO | WO9413358 A1 | 6/1994 |
| WO | WO9604860 A1 | 2/1996 |
| WO | WO199725916 A1 | 7/1997 |
| WO | WO199725917 A1 | 7/1997 |
| WO | WO199736541 A1 | 10/1997 |
| WO | 1997045156 A2 | 12/1997 |
| WO | WO199858681 A2 | 12/1998 |
| WO | 1999009879 A1 | 3/1999 |
| WO | WO1999027862 A1 | 6/1999 |
| WO | WO9953853 A1 | 10/1999 |
| WO | WO2000029062 A2 | 5/2000 |
| WO | WO200158372 A1 | 8/2001 |
| WO | WO2001064145 A1 | 9/2001 |
| WO | WO2001068173 A2 | 9/2001 |
| WO | WO0174252 A2 | 10/2001 |
| WO | WO0180755 A2 | 11/2001 |
| WO | WO0205868 A2 | 1/2002 |
| WO | WO2002005868 A2 | 1/2002 |
| WO | WO2002009599 A2 | 2/2002 |
| WO | WO2002019934 A1 | 3/2002 |
| WO | WO200247569 A1 | 6/2002 |
| WO | WO2002102234 A2 | 12/2002 |
| WO | WO2003039338 A2 | 5/2003 |
| WO | WO2007079278 A1 | 7/2007 |
| WO | 2008003058 A2 | 1/2008 |
| WO | WO2008046031 A2 | 4/2008 |
| WO | WO2008118992 A1 | 10/2008 |
| WO | WO2009032421 A2 | 3/2009 |
| WO | 2009048824 A1 | 4/2009 |
| WO | 2009048943 A1 | 4/2009 |
| WO | 2010054409 A1 | 5/2010 |
| WO | WO2010056771 A1 | 5/2010 |
| WO | 2010082146 A1 | 7/2010 |
| WO | 2011008444 A1 | 1/2011 |
| WO | 2011033421 A1 | 3/2011 |
| WO | WO2011024133 A1 | 3/2011 |
| WO | WO2011089537 A1 | 7/2011 |

(56) References Cited

FOREIGN PATENT DOCUMENTS

| WO | 2011101778 A1 | 8/2011 |
|---|---|---|
| WO | WO2011095937 A1 | 8/2011 |
| WO | 2012001595 A1 | 1/2012 |
| WO | WO2012001595 A1 | 1/2012 |
| WO | WO2012049621 A1 | 4/2012 |
| WO | WO2012066430 A1 | 5/2012 |
| WO | 2012135703 A2 | 10/2012 |
| WO | 2012161880 A1 | 11/2012 |
| WO | WO2012151301 A1 | 11/2012 |
| WO | 2012166239 A1 | 12/2012 |
| WO | 2013040201 A2 | 3/2013 |
| WO | 2013040297 A1 | 3/2013 |
| WO | 2014036439 A2 | 3/2014 |
| WO | 2014058375 A2 | 4/2014 |
| WO | 2014072879 A2 | 5/2014 |
| WO | 2014152575 A2 | 9/2014 |
| WO | 2015143061 A1 | 9/2015 |
| WO | 2015183635 A1 | 12/2015 |

OTHER PUBLICATIONS

International Search Report and Written Opinion issued in PCT/US2015/066874, dated Apr. 1, 2016, 11 pages.
Extended European Search Report issued in EP Application 16182627.6, dated Nov. 8, 2016, 5 pages.
International Preliminary Report on Patentability issued in PCT/US2015/031591, dated Dec. 6, 2016, 7 pages.
International Search Report and Written Opinion issued in PCT/US2016/028006 dated Jul. 12, 2016, 12 pages.
International Preliminary Report on Patentability issued in PCT/US2015/055173, dated Apr. 27, 2017, 7 pages.
International Preliminary Report on Patentability issued in PCT/US2015/066874, dated Jun. 29, 2017, 7 pages.
Extended European Search Report issued in EP Application No. 15174537.9, dated Mar. 2, 2016, 7 pages.
Goldberg, S. Nahum et al., "Variables Affecting Proper System Grounding for Radiofrequency Ablation in an Animal Model", JVIR, vol. 11, No. 8, Sep. 2000, pp. 1069-1075.
Haverkamp, W., et. al. Coagulation of Ventricular Myocardium Using Radiofrequency Alternating Current: Bio-Physical Aspects and Experimental Findings. PACE, 12:187-195, Jan. 1989, Part II.
International Preliminary Examination Report issued in PCT/US2013/060612, completed Mar. 24, 2015, 10 pages.
International Preliminary Report on Patentability issued in PCT/US2008/058324, dated Sep. 29, 2009, 9 pages.
International Preliminary Report on Patentability issued in PCT/US2012/055155, dated Mar. 18, 2014, 11 pages.
International Preliminary Report on Patentability issued in PCT/US2012/055309, dated Mar. 18, 2014, 8 pages.
International Preliminary Report on Patentability issued in PCT/US2013/056211, completed Feb. 24, 2015, 5 pages.
International Preliminary Report on Patentability issued in PCT/US2013/058105, completed Mar. 10, 2015.
International Preliminary Report on Patentability issued in PCT/US2013/060194, dated Mar. 24, 2015, 6 pages.
International Preliminary Report on Patentability issued in PCT/US2014/027491, dated Sep. 24, 2015, 12 pages.
International Preliminary Report on Patentablity issued in PCT/US2013/060183, dated Mar. 24, 2015, 6 pages.
International Search Report and Written Opinion issued in PCT/US2008/058324, dated Aug. 18, 2008, 11 pages.
International Search Report and Written Opinion issued in PCT/US2012/031819, dated Sep. 27, 2012, 16 pages.
International Search Report and Written Opinion issued in PCT/US2012/055155, dated Mar. 11, 2013, 19 pages.
International Search Report and Written Opinion issued in PCT/US2012/055309, dated Nov. 19, 2012, 13 pages.
International Search Report and Written Opinion issued in PCT/US2012/072061, dated Mar. 21, 2013, 9 pages.
International Search Report and Written Opinion issued in PCT/US2013/020503, dated Mar. 20, 2013, 10 pages.
International Search Report and Written Opinion issued in PCT/US2013/021013, dated Apr. 5, 2013, 14 pages.
International Search Report and Written Opinion issued in PCT/US2013/056211, dated Jan. 20, 2014.
International Search Report and Written Opinion issued in PCT/US2013/058105, dated Nov. 22, 2013, 16 pages.
International Search Report and Written Opinion issued in PCT/US2013/060183, dated Jan. 27, 2014, 10 pages.
International Search Report and Written Opinion issued in PCT/US2013/060194, dated Jan. 29, 2014.
International Search Report and Written Opinion issued in PCT/US2013/060194, dated Jan. 29, 2014, 10 pages.
International Search Report and Written Opinion issued in PCT/US2013/060612, dated Feb. 28, 2014, 16 pages.
International Search Report and Written Opinion issued in PCT/US2014/027491, dated Sep. 23, 2014, 17 pages.
International Search Report and Written Opinion issued in PCT/US2015/021300, dated Jun. 9, 2015, 11 pages.
International Search Report and Written Opinion issued in PCT/US2015/055173, dated Jan. 18, 2016, 11 pages.
International Search Report and Written Opinion issued in PCT/US2015/057242, dated Jan. 15, 2016, 11 pages.
International Search Report and Written Opinion issued in PCTUS2015/031591, dated Aug. 17, 2015, 11 pages.
Invitation to Pay Additional Fees and Partial International Search Report issued in PCT/US2014/027491, dated Jul. 28, 2014, 5 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.
Partial International Search Report issued in PCT/US2012/055155, dated Dec. 20, 2012, 7 pages.
Patriciu, A. et al., "Detecting Skin Burns Induced by Surface Electrodes", published in Engineering in Medicine and Biology Society, 2001. Proceedings of the 23rd Annual International Conference of the IEEE, vol. 3, pp. 3129-3131.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Pires, L. A., et al. Temperature-guided Radiofrequency Catheter Ablation of Closed-Chest Ventricular Myocardium with a Novel Thermistor-Tipped Catheter. American Heart Journal, 127(6):1614-1618, Jun. 1994.
Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radiofrequency Lesions in the Voltage and Frequency Domains", Heart Rhythm 2010, 31st Annual Scientific Sessions, May 12-15 in Denver Colorado.
Ring, E. R., et. al. Catheter Ablation of the Ventricular Septum with Radiofrequency Energy. American Heart Journal, 117(6):1233-1240, Jun. 1989.
Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.
Zachary, J.M. et al., "PO4-86 Pin Electrodes Provide Enhanced Resolution Enabling Titration of Radiofrequency Duration to Lesion Maturation", Heart Rhythm 2011, 32 Annual Scientific Sessions, May 4-7, San Francisco, CA.
International Preliminary Report on Patentability issued in PCT/US2015/057242, dated May 4, 2017, 7 pages.
Partial European Search Report issued in EP Application 18177491.0, dated Jul. 16, 2018, 11 pages.

(56) References Cited

OTHER PUBLICATIONS

Extended European Search Report issued in EP18177491.0, dated Oct. 26, 2018, 10 pages.

* cited by examiner

MEDICAL DEVICES WITH A FLEXIBLE ELECTRODE ASSEMBLY COUPLED TO AN ABLATION TIP

CROSS-REFERENCE TO RELATED APPLICATION

This application claims priority to Provisional Application No. 62/068,334, filed Oct. 24, 2014, which is herein incorporated by reference in its entirety.

TECHNICAL FIELD

The present disclosure pertains to medical devices, and methods for manufacturing medical devices. More particularly, the present disclosure pertains to for cardiac mapping and/or ablation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example catheter may include a catheter for use in cardiac mapping and/or ablation. The catheter comprises:
  an elongate catheter shaft having a distal ablation electrode region;
  an electrode assembly coupled to the distal ablation electrode region; and
  wherein the electrode assembly includes a flexible circuit having one or more electrodes disposed thereon.

Alternatively or additionally to any of the embodiments above, the distal ablation electrode region has an opening formed therein and wherein the electrode assembly extends through the opening.

Alternatively or additionally to any of the embodiments above, the electrode assembly includes a region that is disposed along a distal end of the distal ablation electrode region.

Alternatively or additionally to any of the embodiments above, the electrode assembly includes a plurality of arm regions and wherein each of the arm regions includes at least one electrode.

Alternatively or additionally to any of the embodiments above, the electrode assembly includes three or more arm regions.

Alternatively or additionally to any of the embodiments above, the electrode assembly includes four or more arm regions.

Alternatively or additionally to any of the embodiments above, the electrode assembly includes a mechanical locking end region that is capable of mechanically securing the electrode assembly to the distal ablation electrode region.

Alternatively or additionally to any of the embodiments above, the distal ablation electrode region has an opening formed therein and wherein the mechanical locking end region extends through the opening.

Alternatively or additionally to any of the embodiments above, the catheter shaft includes an inner channel, wherein the distal ablation electrode region includes a first opening and a second opening, and wherein the electrode assembly extends along the inner channel, through the first opening, along an outer surface of the distal ablation electrode region, and through the second opening.

Alternatively or additionally to any of the embodiments above, the electrode assembly is adhesively bonded to the distal ablation electrode region.

Alternatively or additionally to any of the embodiments above, the electrode assembly includes one or more electrode regions and one or more electrically insulated regions.

Alternatively or additionally to any of the embodiments above, the electrode assembly extends circumferentially around the distal ablation electrode region.

Alternatively or additionally to any of the embodiments above, the electrode assembly is designed to bow radially outward from the distal ablation electrode region.

Alternatively or additionally to any of the embodiments above, the distal ablation electrode region includes a platinum ablation tip electrode.

Methods for manufacturing a medical device are also disclosed. The methods may comprise:
  inserting an electrode assembly into a channel formed within a distal ablation tip of a catheter;
  wherein the electrode assembly includes a flexible circuit having one or more electrodes disposed thereon;
  wherein the distal ablation tip includes a first opening and a second opening; and
  extending the electrode assembly extends through the first opening, along an outer surface of the distal ablation tip, and through the second opening.

Another embodiment of a catheter for use in cardiac mapping and/or ablation may comprise:
  an elongate catheter shaft having an inner channel and a distal end region;
  a distal ablation tip capable of ablating tissue disposed at the distal end region;
  an electrode assembly coupled to the distal ablation tip;
  wherein the electrode assembly includes a flexible circuit having one or more electrodes disposed thereon;
  wherein the distal ablation electrode region includes a first opening and a second opening;
  wherein the electrode assembly extends along the inner channel, through the first opening, along an outer surface of the distal ablation tip, and through the second opening.

Alternatively or additionally to any of the embodiments above, the electrode assembly includes a region that is disposed along a distal end of the distal ablation tip.

Alternatively or additionally to any of the embodiments above, the electrode assembly includes a plurality of arm regions and wherein each of the arm regions includes at least one electrode.

Alternatively or additionally to any of the embodiments above, the electrode assembly includes a mechanical locking end region that is capable of mechanically securing the electrode assembly to the distal ablation tip.

Alternatively or additionally to any of the embodiments above, the mechanical locking end region extends through the first opening, the second opening, or both.

The above summary of some embodiments is not intended to describe each disclosed embodiment or every implementation of the present disclosure. The Figures, and Detailed Description, which follow, more particularly exemplify these embodiments.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The disclosure may be more completely understood in consideration of the following detailed description in connection with the accompanying drawings, in which.

Figure 1:
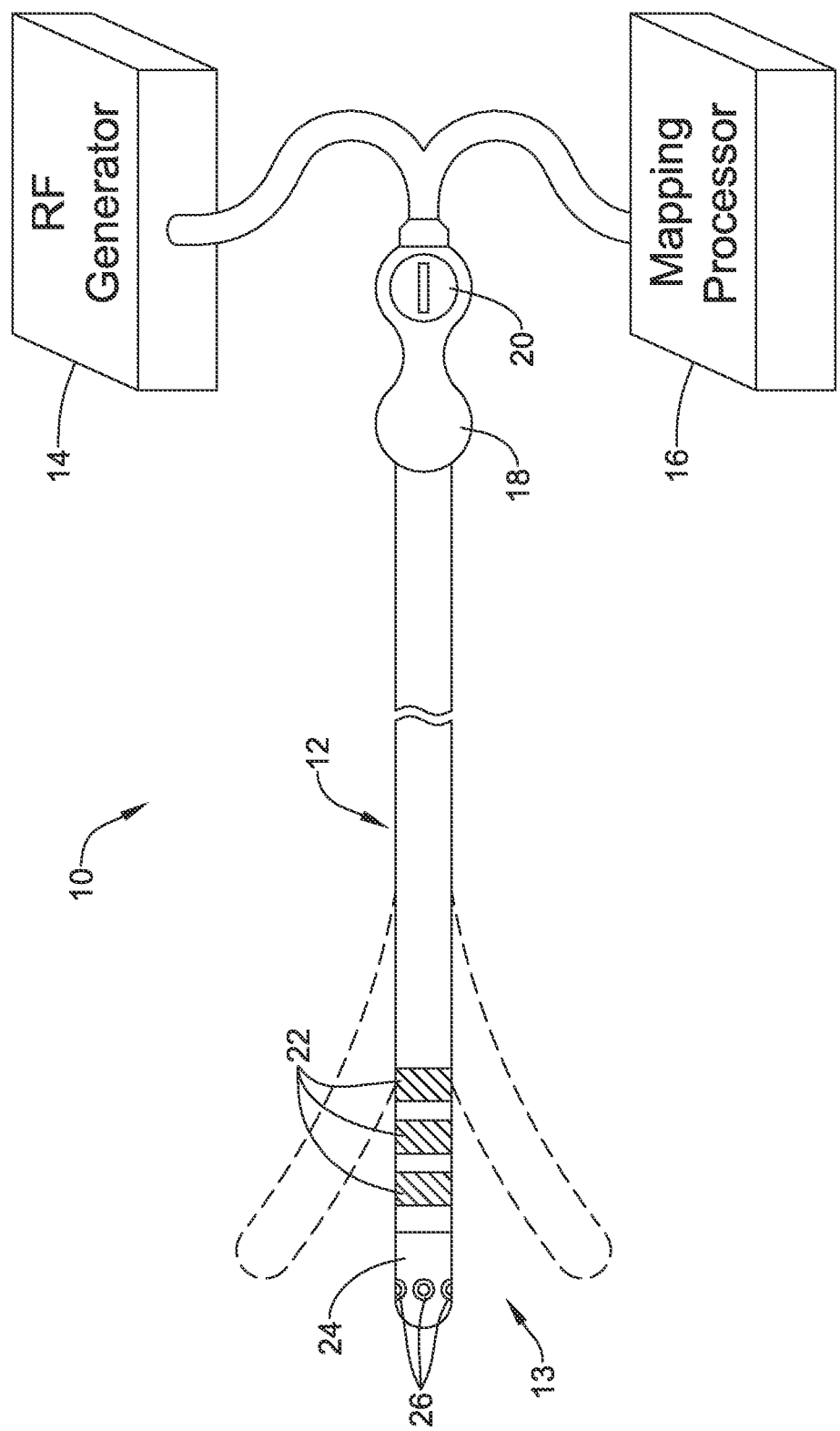
FIG. 1 is a plan view of an example cardiac mapping and/or ablation system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example cardiac mapping and/or ablation system 10. As shown in FIG. 1, system 10 may include an elongated member or catheter shaft 12, an RF generator 14, and a processor 16 (e.g., a mapping processor, ablation processor, and/or other processor). Illustratively, shaft 12 may be operatively coupled to at least one or more (e.g., one or both) of RF generator 14 and processor 16. Alternatively, or in addition, a device, other than shaft 12, that may be utilized to apply ablation energy to and/or map a target area, may be operatively coupled to at least one or more of RF generator 14 and processor 16. RF generator 14 may be capable of delivering and/or may be configured to deliver ablation energy to shaft 12 in a controlled manner in order to ablate target area sites identified by processor 16. Although the processor 16 and RF generator 14 may be shown as discrete components, these components or features of components may be incorporated into a single device. System 10 may include any of one or more other features, as desired.

In at least some embodiments, shaft 12 may include a handle 18, which may have an actuator 20 (e.g., a control knob or other actuator). The handle 18 (e.g., a proximal handle) may be positioned at a proximal end of shaft 12, for example. Illustratively, shaft 12 may include a flexible body having a having a distal portion which may include the one or more electrodes. For example, the distal portion of shaft 12 may include one or more of a plurality of ring electrodes 22, a distal ablation tip electrode 24, and a plurality of micro-electrodes or micro-electrode assemblies 26 disposed or otherwise positioned within and/or electrically isolated from distal ablation tip electrode 24.

Shaft 12 may be steerable to facilitate navigating the vasculature of a patient or navigating other lumens. Illustratively, a distal portion 13 of shaft 12 may be deflected by manipulation of actuator 20 to effect steering shaft 12. In some instances, distal portion 13 of shaft 12 may be deflected to position distal ablation tip electrode 24 and/or micro-electrode assemblies 26 adjacent target tissue or to position the distal portion 13 of shaft 12 for another suitable purpose. Additionally, or alternatively, distal portion 13 of shaft 12 may have a pre-formed shape adapted to facilitate positioning distal ablation tip electrode 24 and/or micro-electrode assemblies 26 adjacent a target tissue. Illustratively, the preformed shape of distal portion 13 of shaft 12 may be a radiused shape (e.g., a generally circular shape or a generally semi-circular shape) and/or may be oriented in a plane transverse to a general longitudinal direction of shaft 12. These are just examples.

In some instances, system 10 may be utilized in ablation procedures on a patient. Illustratively, shaft 12 may be configured to be introduced into or through vasculature of a patient and/or into or through any other lumen or cavity. In one example, shaft 12 may be inserted through the vasculature of the patient and into one or more chambers of the patient's heart (e.g., a target area). When in the patient's vasculature or heart, shaft 12 may be used to map and/or ablate myocardial tissue using the ring electrodes 22, micro-electrode assemblies 26, and/or distal ablation tip electrode 24. In some instances, distal ablation tip electrode 24 may be configured to apply ablation energy to myocardial tissue of the heart of a patient.

In some instances, micro-electrode assemblies 26 may be circumferentially distributed about a distal ablation tip electrode 24. In some instances, system 10 may not include distal ablation tip electrode 24 and, in such embodiments, micro-electrode assemblies 26 may be circumferentially distributed about shaft 12 (e.g., along a distal tip of shaft 12). In general, micro-electrode assemblies 26, as their name suggests, are relatively small in size (e.g., smaller than distal ablation tip electrode 24). Micro-electrode assemblies 26 may be capable of operating, or configured to operate, in unipolar or bipolar sensing modes. In some cases, micro-electrode assemblies 26 may define and/or at least partially form one or more bipolar microelectrode pairs. In an illustrative instance, shaft 12 may have three micro-electrode assemblies 26 distributed about the circumference of distal ablation tip electrode 24, such that the circumferentially spaced microelectrodes may form respective bipolar microelectrode pairs. Each bipolar microelectrode pair may be capable of generating, or may be configured to generate, an output signal corresponding to a sensed electrical activity (e.g., an electrogram (EGM) reading) of the myocardial tissue proximate thereto. Additionally or alternatively to the circumferentially spaced micro-electrode assemblies 26, shaft 12 may include one or more forward facing micro-electrode assemblies 26 (not shown). The forward facing micro-electrode assemblies 26 may be generally centrally located within distal ablation tip electrode 24 and/or at an end of a tip of shaft 12.

In some examples, micro-electrode assemblies 26 may be operatively coupled to processor 16 and the generated output signals from micro-electrode assemblies 26 may be sent to the processor 16 of ablation system 10 for processing in one or more manners discussed herein and/or for processing in other manners. Illustratively, an EGM reading or signal of an output signal from a bipolar microelectrode pair may at least partially form the basis of a contact assessment, ablation area assessment (e.g., tissue viability assessment), and/or an ablation progress assessment (e.g., a lesion formation/maturation analysis), as discussed below.

Distal ablation tip electrode 24 may be a suitable length and may have a suitable number of micro-electrode assemblies 26 positioned therein and spaced circumferentially and/or longitudinally about distal ablation tip electrode 24. In some instances, distal ablation tip electrode 24 may have a length of between one (1) mm and twenty (20) mm, three (3) mm and seventeen (17) mm, or six (6) mm and fourteen (14) mm. In one illustrative example, distal ablation tip electrode 24 may have an axial length of about eight (8) mm. Distal ablation tip electrode 24 may be formed from other otherwise include platinum and/or other suitable materials. These are just examples.

Processor 16 may be capable of processing or may be configured to process the electrical signals of the output signals from micro-electrode assemblies 26 and/or ring electrodes 22. Based, at least in part, on the processed output signals from micro-electrode assemblies 26 and/or ring electrodes 22, processor 16 may generate an output to a display (not shown) for use by a physician or other user. In instances where an output is generated to a display and/or other instances, processor 16 may be operatively coupled to or otherwise in communication with the display. Illustratively, the display may include various static and/or dynamic information related to the use of system 10. In one example, the display may include one or more of an image of the target area, an image of shaft 12, and information related to EGMs, which may be analyzed by the user and/or by a processor of system 10 to determine the existence and/or location of arrhythmia substrates within the heart, to determine the location of shaft 12 within the heart, and/or to make other determinations relating to use of shaft 12 and/or other elongated members.

System 10 may include an indicator in communication with processor 16. The indicator may be capable of providing an indication related to a feature of the output signals received from one or more of the electrodes of shaft 12. In one example of an indicator, an indication to the clinician about a characteristic of shaft 12 and/or the myocardial tissue interacted with and/or being mapped may be provided on the display. In some cases, the indicator may provide a visual and/or audible indication to provide information concerning the characteristic of shaft 12 and/or the myocardial tissue interacted with and/or being mapped.

Figure 2:
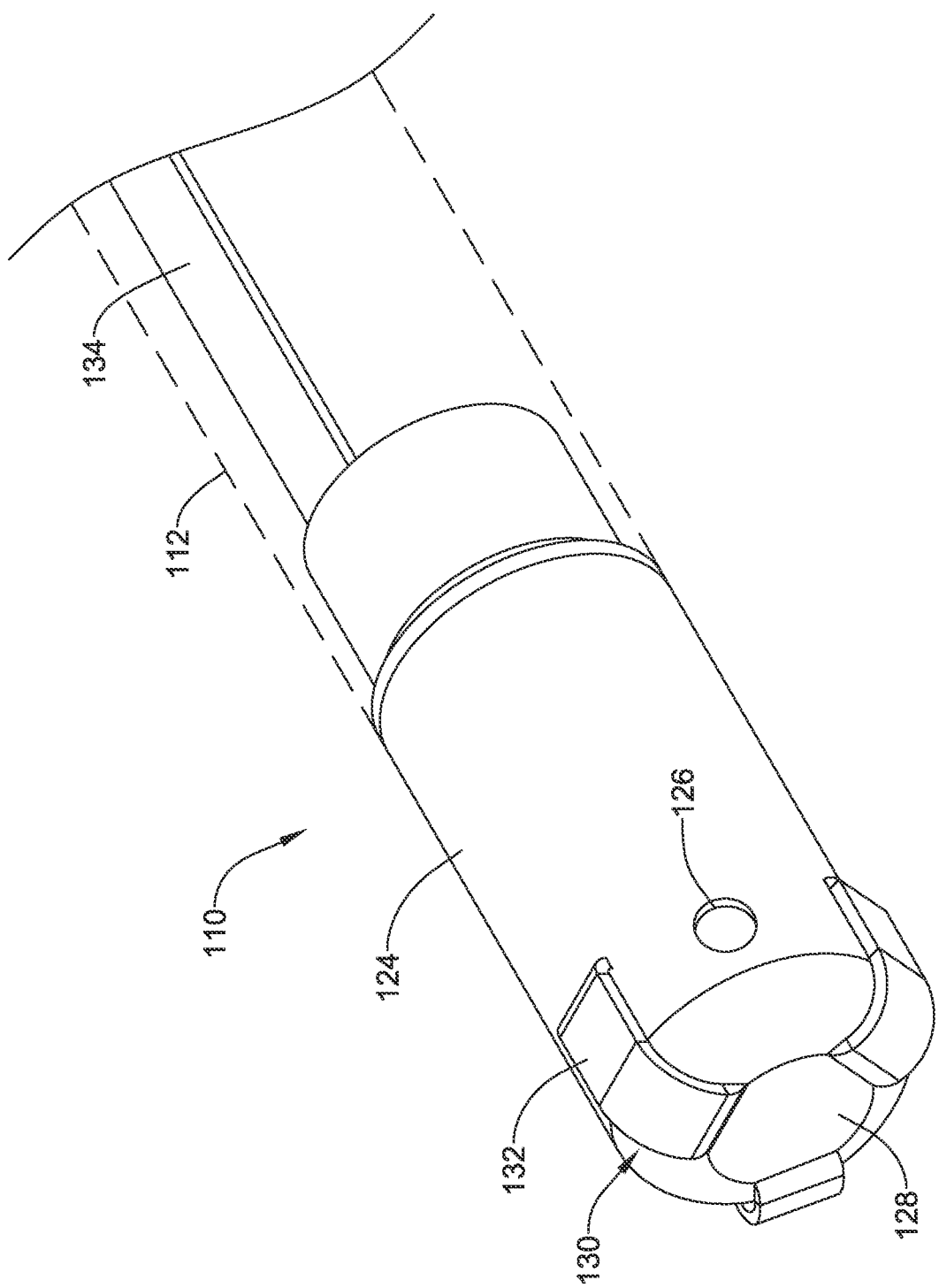
FIG. 2 is a partially cutaway perspective view of a portion of an example cardiac mapping and/or ablation system.

FIG. 2 illustrates another example system 110 that may be similar in form and function to other systems disclosed herein. System 110 may include catheter shaft 112. Distal ablation tip electrode 124 may be disposed at the distal end of catheter shaft 112. Distal ablation tip electrode 124 may include one or more irrigation ports. For example, distal ablation tip electrode 124 may include one or more circumferential irrigation ports 126. In some of these and in other instances, distal ablation tip electrode 124 may also include a distal irrigation port 128. In uses where irrigation is not desired/needed, ports 126/128 may be omitted or sealed, for example with an epoxy.

In some instances, one or more micro-electrode assemblies (e.g., similar to micro-electrode assemblies 26) may be disposed along distal ablation tip electrode 124. In some of these and in other embodiments, an electrode assembly 130 may be coupled to distal ablation tip electrode 124. Electrode assembly 130 may include one or more electrodes or electrode regions 132. Electrodes 132 may include monopolar electrodes, one or more pairs of bipolar electrodes, or combinations thereof. Electrodes 132 may also take the form of sensors such as impedance and/or contact sensors. A proximal connector 134 may be disposed along (e.g., within) catheter shaft 112. Proximal connector 134 may be used to connect electrode assembly 130 with a suitable processor/generator.

The use of electrode assembly 130 may be desirable for a number of reasons. For example, electrode assembly 130 may allow for electrodes 132 to be disposed at the front face or distal end of distal ablation tip 124. This may allow electrodes 132 to be used to sense contact between distal ablation tip 124 and a target tissue. In addition, because it may have a relatively small, compact shape, the use of electrode assembly 130 may free up additional space along and/or within distal ablation tip 124 for other useful structures such as micro-electrodes, force sensors, contact sensors, magnetic sensors, or the like. Moreover, electrode assembly 130 may be wrapped or otherwise disposed along distal ablation tip 124 in a manner that reduces protruding edges that could catch on tissue, other medical devices, etc. Furthermore, by weaving electrode assembly 130 through openings in distal ablation tip 124, RF edge effects may be reduced or minimized.

Electrode assembly 130 may take the form of a flexible circuit. For example, electrode assembly 130 may include a substrate with one or more electrodes (e.g., electrodes 132) disposed thereon. The substrate may include a polymeric material (e.g., such as polyimide or other suitable materials including those disclosed herein). Electrode assembly 130 may include a coating such as a parylene coating or other suitable biocompatible coating. Electrodes 132 may be sputtered onto the substrate with iridium oxide. In some of these and in other embodiments, electrodes 132 may be copper or gold electrodes (or electrodes formed of other suitable materials) disposed along the substrate. In some instances, a temperature or other sensor may be disposed along the substrate. In addition, a magnetic sensing coil, piezoelectric film, MEMS force sensor, or the like may be coupled to assembly 130. Some example flexible circuits that may suitable for use as electrode assembly 130 may include or resemble those disclosed in U.S. Patent Application Pub. No. US 2013/0165926, the entire disclosure of which is herein incorporated by reference. The use of a flex circuit may be desirable by allowing for batch processing at relatively high volumes so that manufacturability of system 110 may be increased.

In some instances, electrode assembly 130 may include an inner insulating layer contacts distal ablation tip 124 and electrically insulates electrode assembly 130 from distal ablation tip 124. Electrodes 132 may be disposed on the insulating layer. Alternatively, electrodes 132 may take the form of a conductive layer or trace disposed along the insulating layer. The conductive layer may extend along essentially the entire length of the insulating layer or along one or more discrete sections thereof. Numerous configurations are contemplated.

Figure 3:
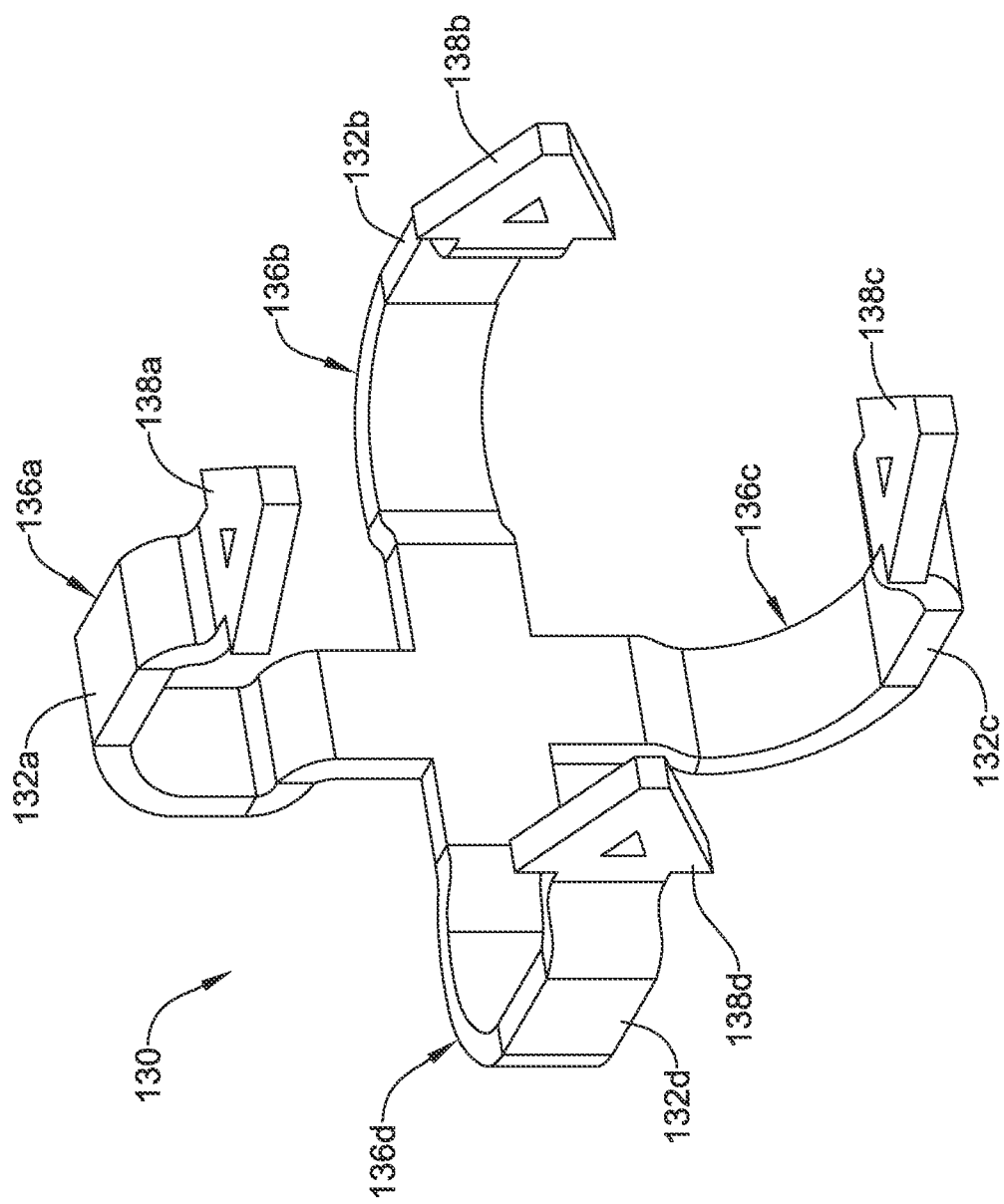
FIG. 3 is a perspective view of an example electrode assembly.

FIG. 3 is a perspective view of electrode assembly 130. Here it can be seen that electrode assembly 130 may include a plurality of arms including arms 136a/136b/136c/136d each having one or more electrodes 132a/132b/132c/132d. Each of arms 136a/136b/136c/136d may include a mechanical interconnecting member 138a/138b/138c/138d. Mechanical interconnecting members 138a/138b/138c/138d may be utilized to secure electrode assembly 130 to system 110 (and/or distal ablation tip 124). In this example, mechanical interconnecting members 138a/138b/138c/138d take the form of arrow-shaped projections with a tapered edge. Such a shape may allow mechanical interconnecting members 138a/138b/138c/138d to be passed through an opening and, by interference, being sufficiently captured within the opening. The precise shape of mechanical interconnecting members 138a/138b/138c/138d may vary and is not intended to be limited to just being arrow-shaped. Mechanical interconnecting members 138a/138b/138c/138d may have a variety of shapes including rounded shapes, geometric shapes, shapes with relief cutouts (e.g., a "split arrow" shape), shapes with flanges and/or projections, shapes that are deformable or reshapable into two or more shapes, or the like. These are just examples. Other shapes are contemplated.

Figure 4:
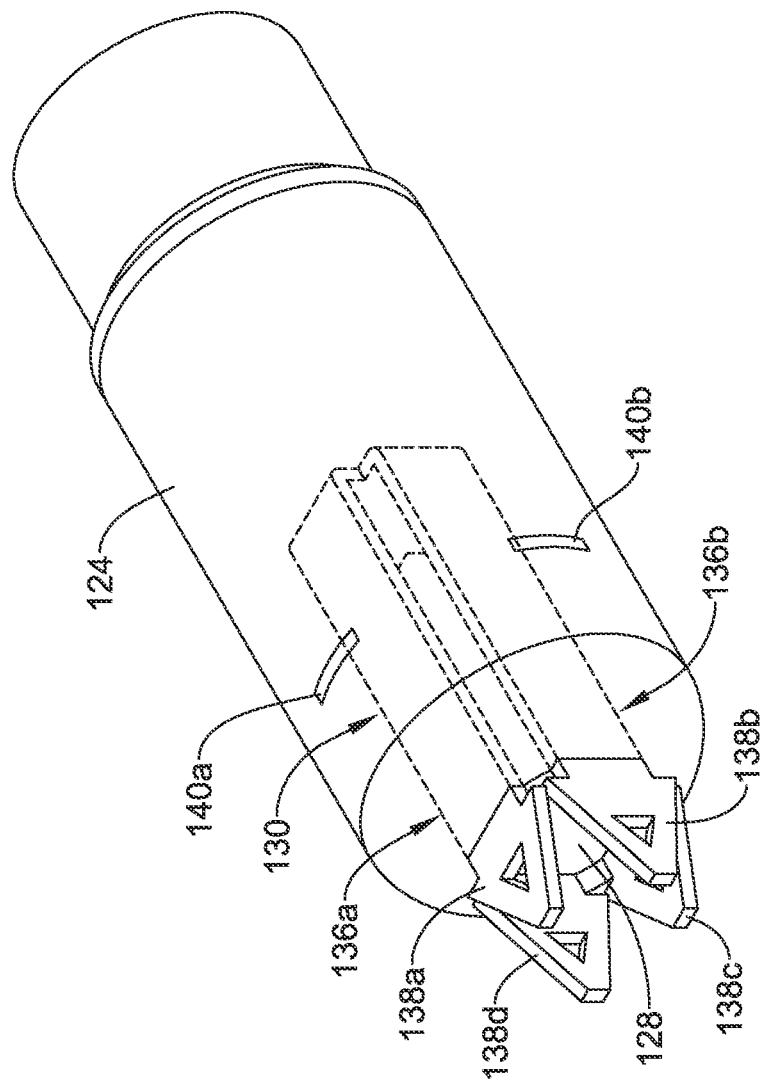
FIGS. 4-6 illustrate an example method for securing an electrode assembly to a cardiac mapping and/or ablation system.
Figure 5:
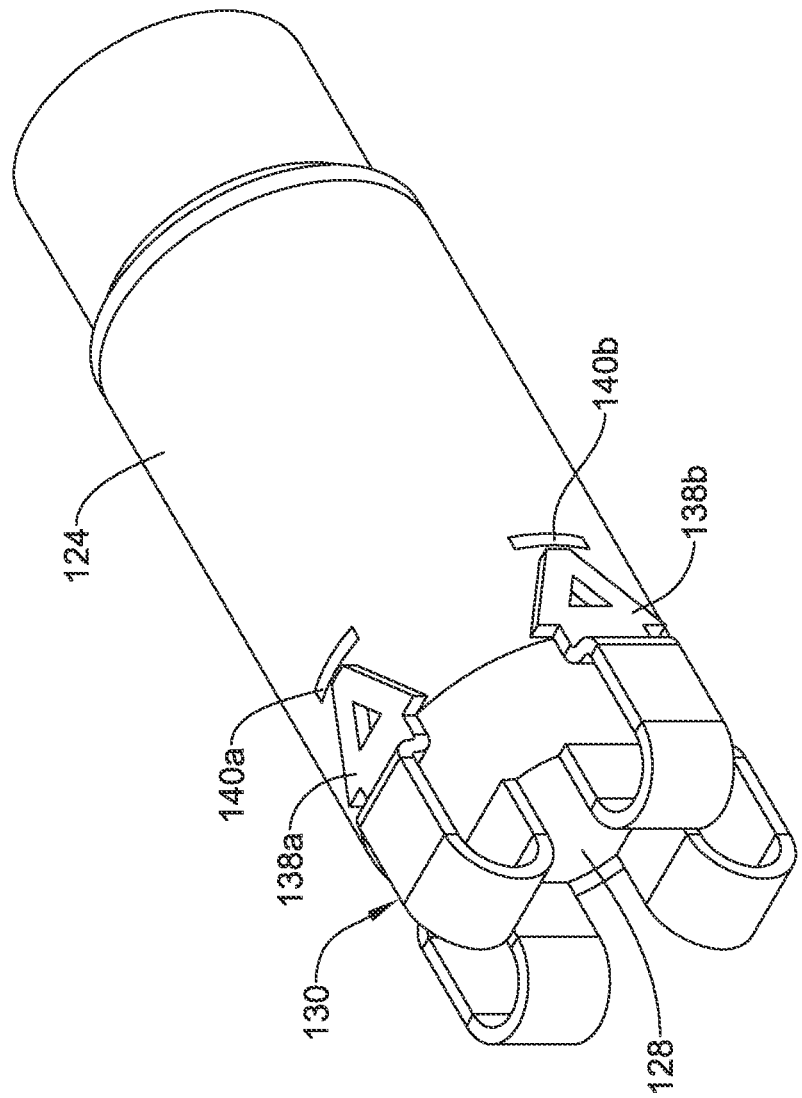
Figure 6:
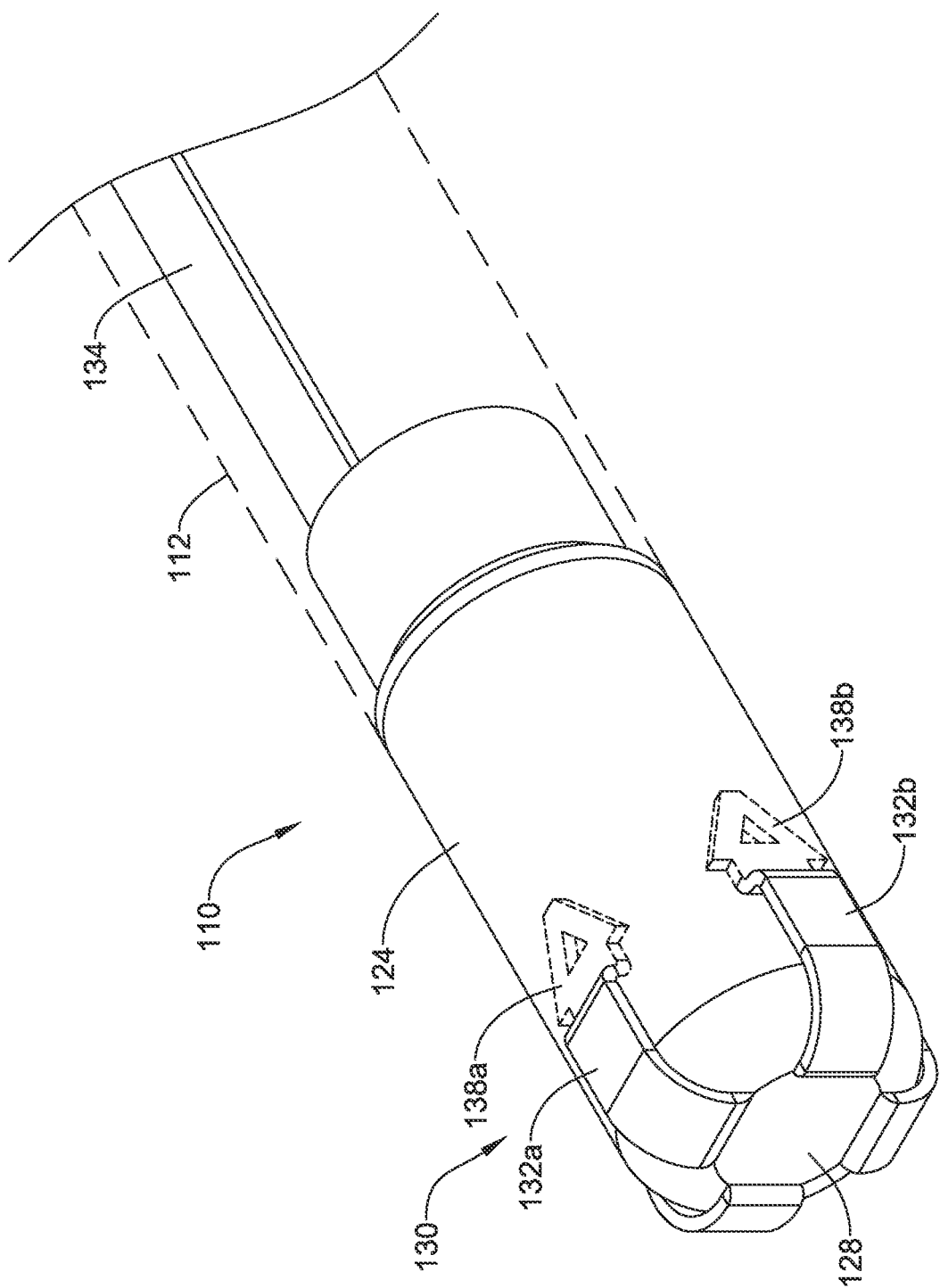

FIGS. 4-6 illustrate an example method for manufacturing and/or assembling system 110. For example, in FIG. 4 it can be seen that electrode assembly 130 may be disposed along an interior of distal ablation tip 124. Arms 136a/136b/136c/136d may be oriented so that mechanical interconnecting member 138a/138b/138c/138d extend through distal irrigation port 128. Arms 136a/136b/136c/136d may be manipulated so that mechanical interconnecting member 138a/138b/138c/138d are folded proximally toward openings 140a/140b as shown in FIG. 5. Openings 140a/140b may be cuts or slots formed in a suitable manner (e.g., laser cutting with chamfer to reduce/minimize abrasion with assembly 130). It can be appreciated that in the views of FIGS. 4-6 only two openings 140a/140b are shown. However, in practice a suitable number of openings may be utilized. For example, four openings may be utilized when electrode assembly 130 includes four arms. Mechanical interconnecting member 138a/138b/138c/138d may be extended into openings 140a/140b (and similar openings not shown in this view) as shown in FIG. 6. This may secure electrode assembly 130 to system 110 (and/or to distal ablation tip 124.

Proximal connector 134 may be coupled to a suitable processor/generator using flying leads, ribbonized cable, or by simply extending proximal connector 134 to the processor/generator. When connecting proximal connector 134 to another suitable device or wire, terminals may be disposed along proximal connector 134. The terminals may be formed by wire bonding, hot bar soldering, anisotropic conductive films, soldering, or the like.

Figure 7:
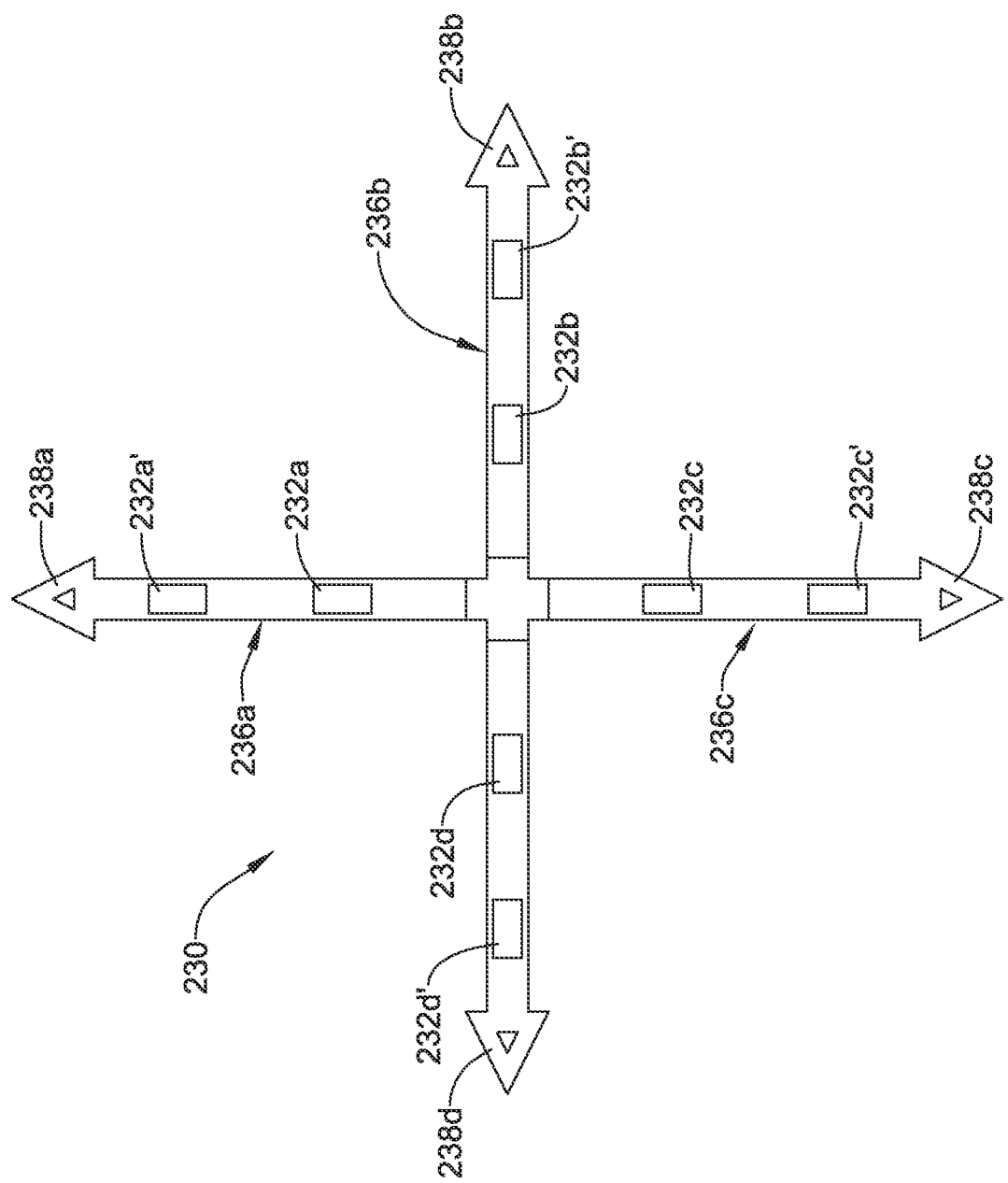
FIG. 7 is a side view of an example electrode assembly.

FIG. 7 illustrates another example electrode assembly 230 that may be similar in form and function to other assemblies disclosed herein and may be used, as appropriate, with the systems disclosed herein. Assembly 230 may include arms 236a/236b/236c/236d. Each of arms 236a/236b/236c/236d may include mechanical interconnecting member 138a/138b/138c/138d. In this example, two electrodes are defined along each of arms 236a/236b/236c/236d. For example, arm 236a may include electrodes 232a/232a', arm 236b may include electrodes 232b/232b', arm 236c may include electrodes 232c/232c', and arm 236d may include electrodes 232d/232d'.

Figure 8:
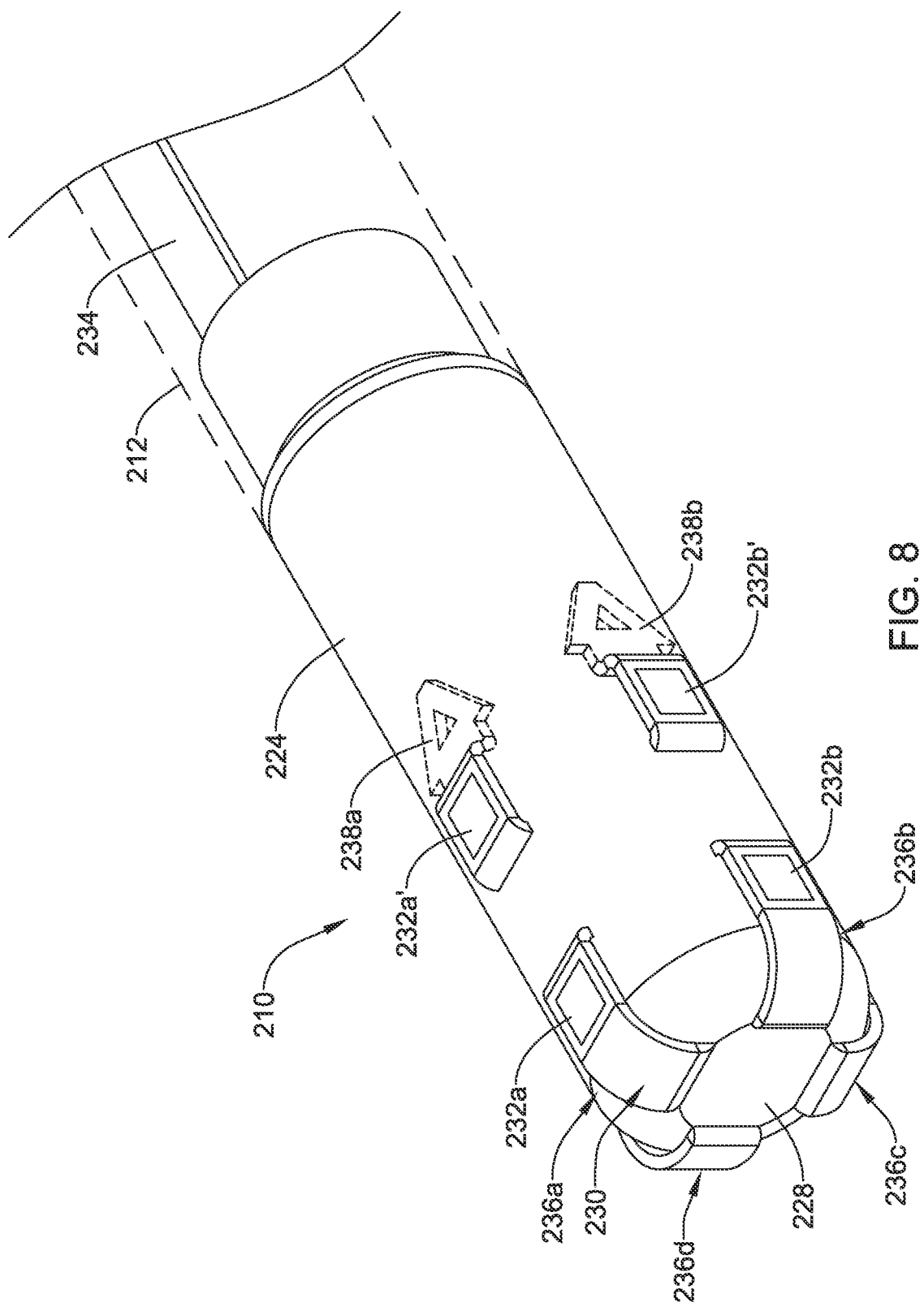
FIG. 8 is a partially cutaway perspective view of a portion of an example cardiac mapping and/or ablation system.

FIG. 8 illustrates system 210. System 210 includes catheter shaft 212. Proximal connector 234 may be disposed along shaft 212 and may be coupled to electrode assembly 230. Electrode assembly 230 may be assembled onto distal ablation tip 224 in a manner similar to what is disclosed herein. For example, arms 236a/236b/236c/236d may be passed through port 228 and woven in and out of a pair of openings along distal ablation tip 224 so that electrodes 232a/232a'/232b/232b'/232c/232c'/232d/232d' are disposed along tip 224. Alternatively, each of arms 236a/236b/236c/236d may be passed through port 228, along the outer surface of distal ablation tip 224, and then through a single opening along distal ablation tip 224. In at least some instances, distal ablation tip 224 takes the form of a distal ablation tip electrode 224.

Figure 9:
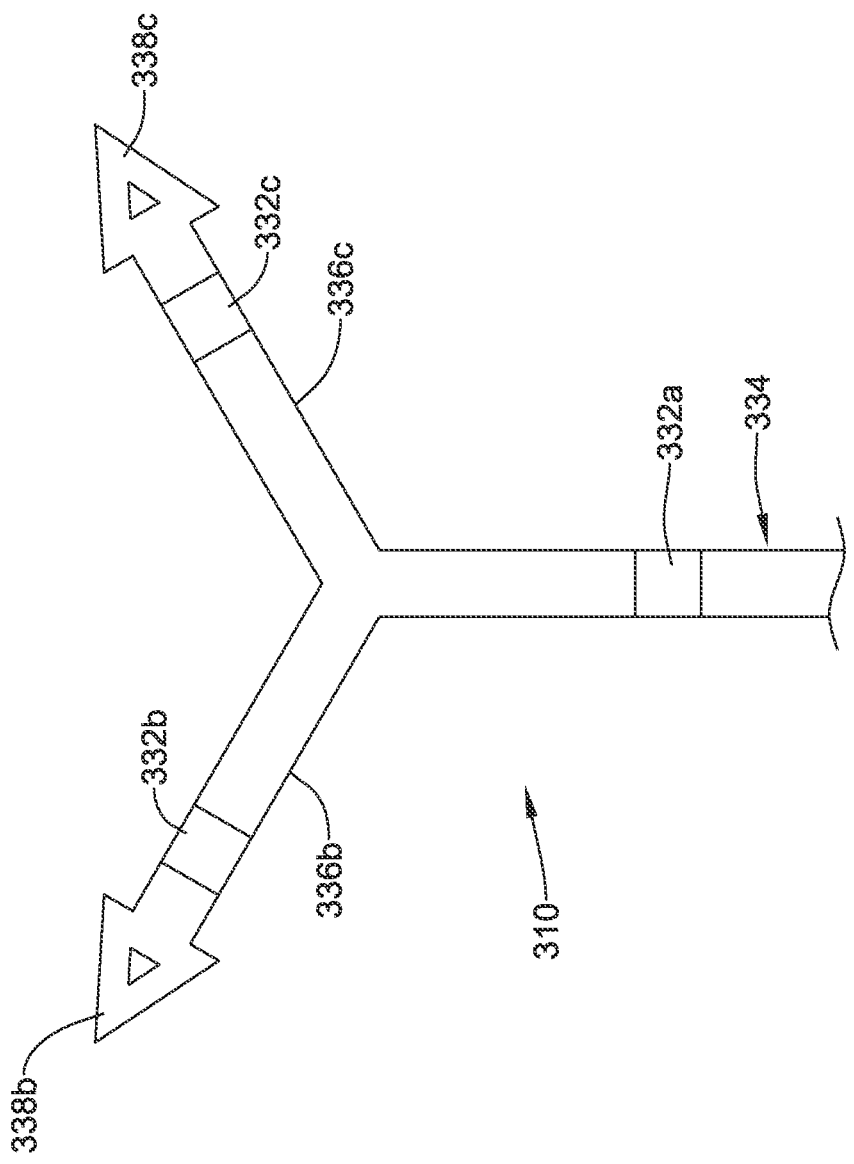
FIG. 9 is a side view of an example electrode assembly.

FIG. 9 illustrates another example electrode assembly 330 that may be similar in form and function to other assemblies disclosed herein and may be used, as appropriate, with the systems disclosed herein. In this embodiment, electrode assembly 330 may include three arms. For example, assembly 330 may include arms 336b/336c and a third arm/connector 334. Each of arms 336b/336c may include mechanical interconnecting member 338b/338c. Each of arms 336b/336c may include electrodes 332b/332c. Connector 334 may also include electrode 332a.

Figure 10:
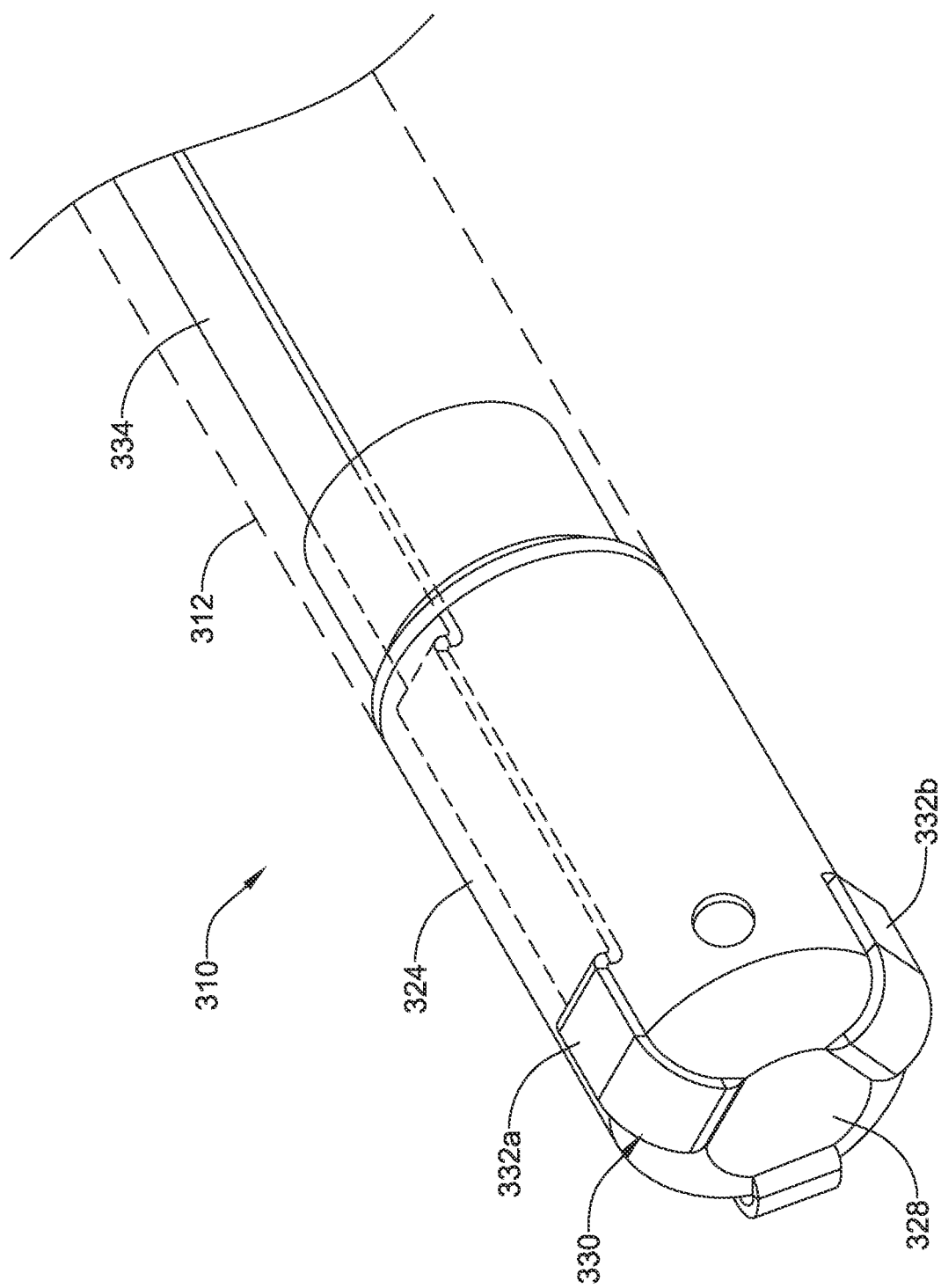
FIG. 10 is a partially cutaway perspective view of a portion of an example cardiac mapping and/or ablation system.

FIG. 10 illustrates system 310. System 310 includes catheter shaft 312. Electrode assembly 330 may be assembled onto distal ablation tip 324 in a manner similar to what is disclosed herein. For example, each of arms 336b/236c and connector 334 may be passed through port 328 and passed through an opening along distal ablation tip 324 so that electrodes 332a/332b/332c are disposed along tip 324. Connector 334 may continue along an inner surface (or an outer surface) of shaft 312 to a location where it may be coupled to a suitable processor/generator. In at least some instances, distal ablation tip 324 takes the form of a distal ablation tip electrode 324.

Figure 11:
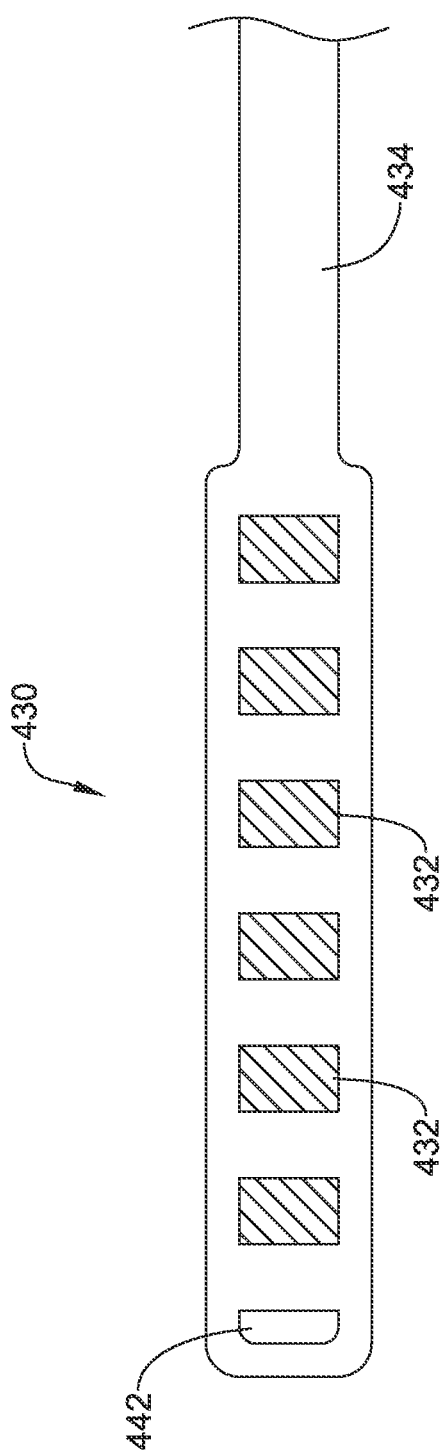
FIG. 11 is a side view of an example electrode assembly.

FIG. 11 illustrates another example electrode assembly 430 that may be similar in form and function to other assemblies disclosed herein and may be used, as appropriate, with the systems disclosed herein. Assembly 430 may include a plurality of electrodes 432. Assembly 430 may also include an opening 442 and proximal connector 434.

Figure 12:
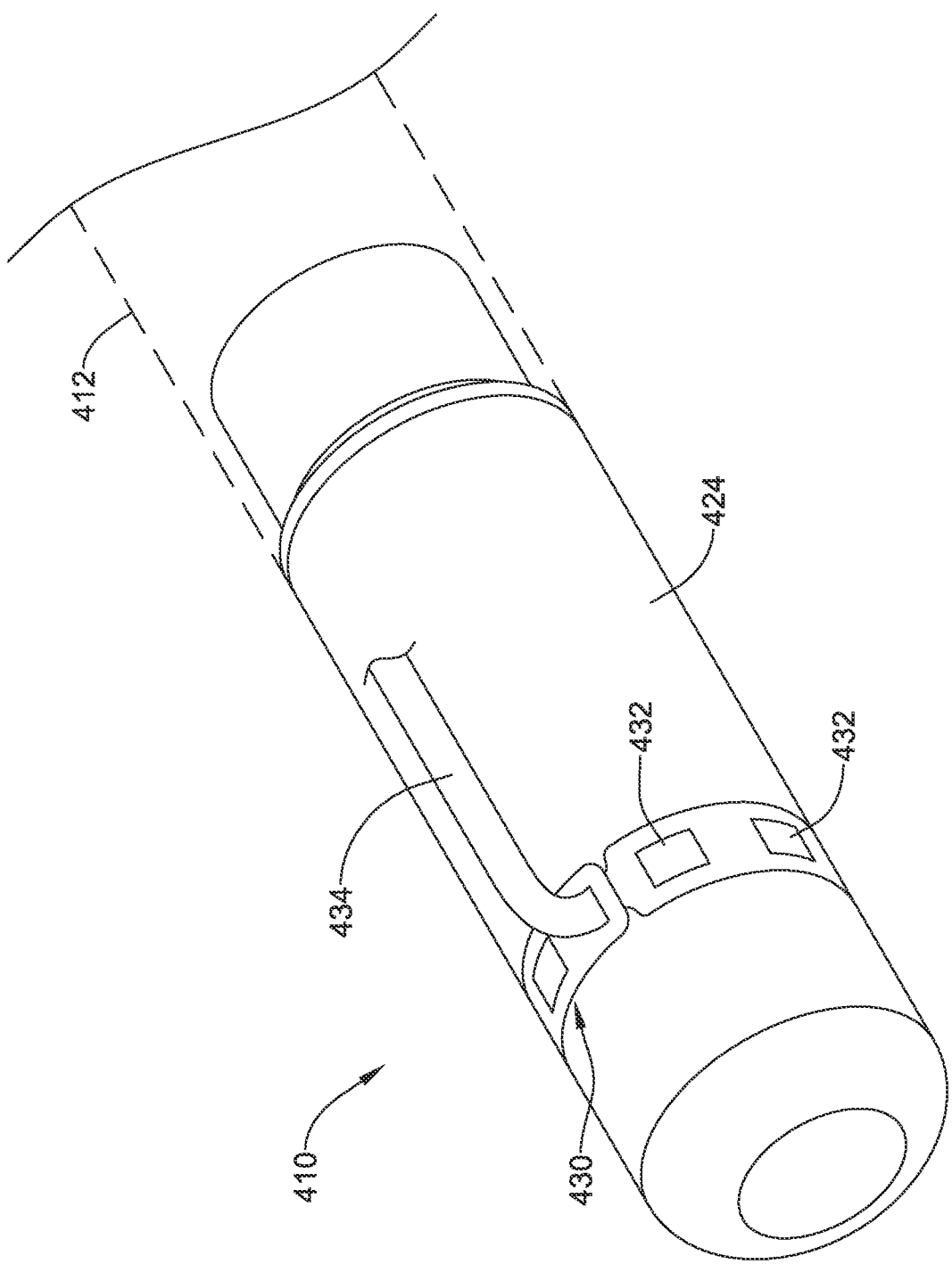
FIG. 12 is a partially cutaway perspective view of a portion of an example cardiac mapping and/or ablation system.

FIG. 12 illustrates system 410. System 410 includes catheter shaft 412. Electrode assembly 430 may be assembled onto distal ablation tip 424 in a manner similar to what is disclosed herein. For example, electrode assembly 430 may take the form of a strip that is designed to extend circumferentially about distal ablation tip 424. Proximal connector 434 may extend through opening 442 and then proximally along shaft 412. This may include extending proximal connector 434 along the outer surface of shaft 412, along the inner surface of shaft 412, or both. In at least some instances, distal ablation tip 424 takes the form of a distal ablation tip electrode 424.

Figure 13:
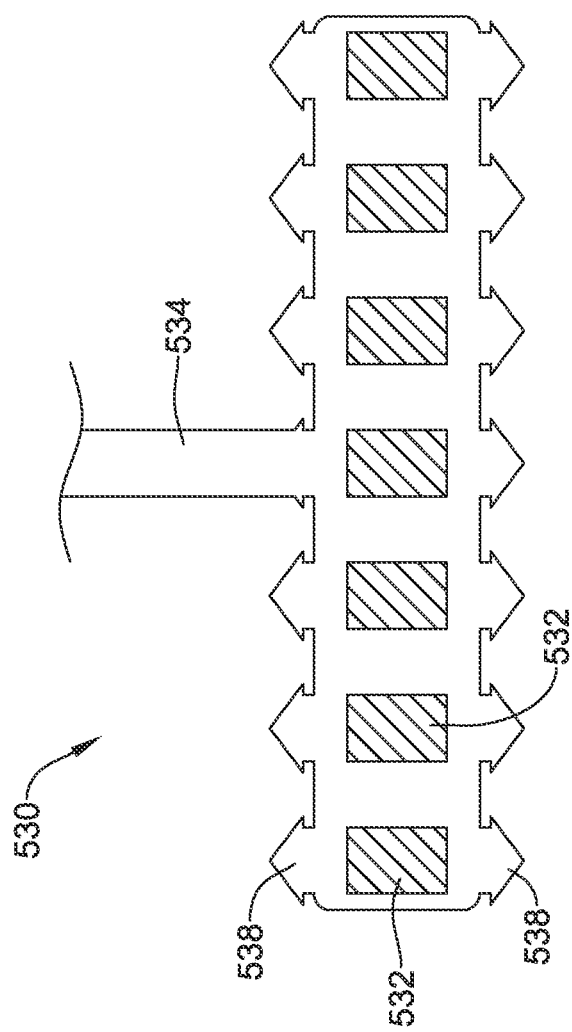
FIG. 13 is a side view of an example electrode assembly.

FIG. 13 illustrates another example electrode assembly 530 that may be similar in form and function to other assemblies disclosed herein and may be used, as appropriate, with the systems disclosed herein. Assembly 530 may include a plurality of electrodes 532. Assembly 530 may also include a plurality of mechanical interconnecting member 538. In this example, a pair of opposing mechanical interconnecting members 538 are positioned on opposite sides of each electrode 532. Assembly 530 may also include proximal connector 534.

Figure 14:
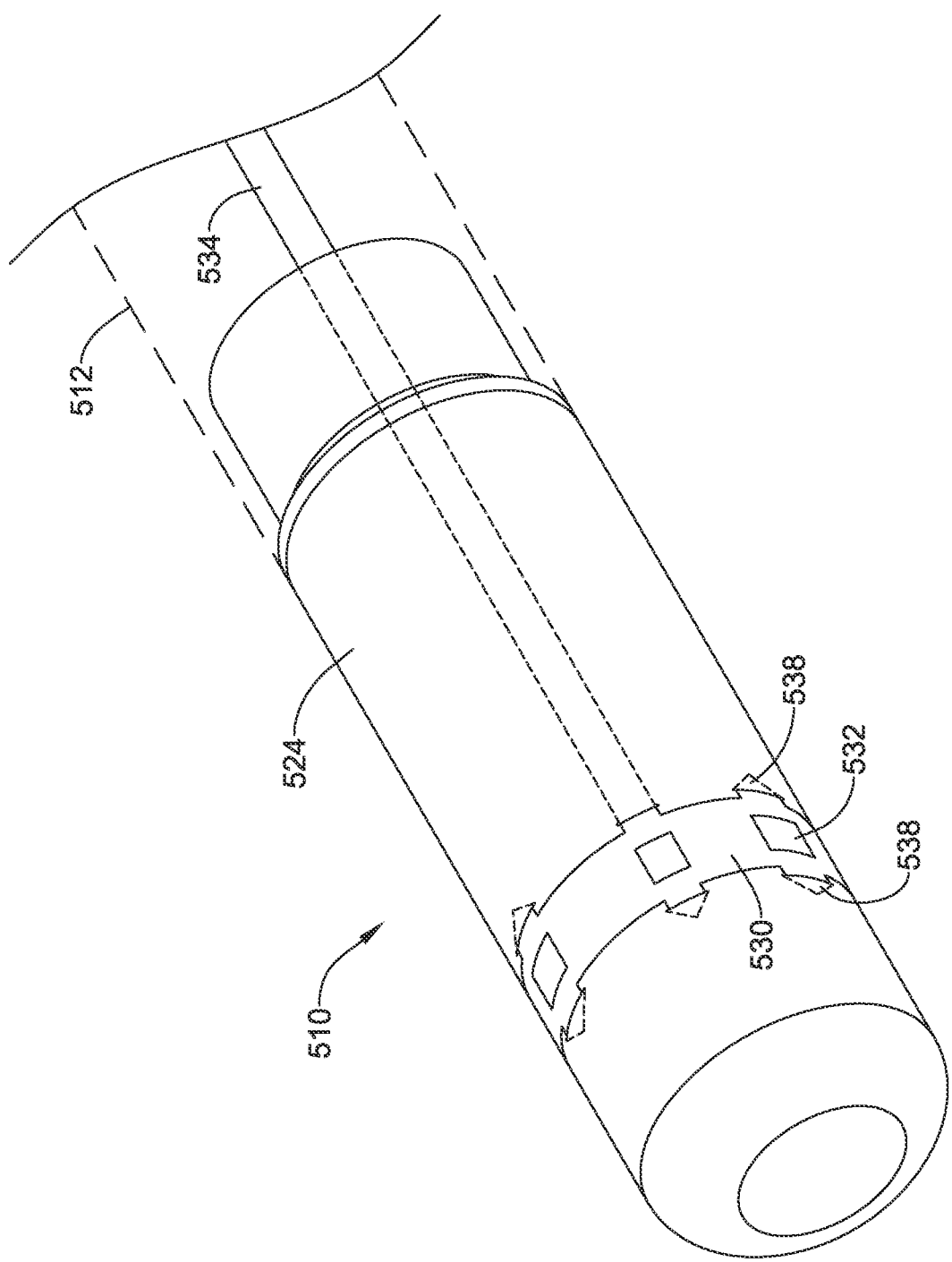
FIG. 14 is a partially cutaway perspective view of a portion of an example cardiac mapping and/or ablation system.

FIG. 14 illustrates system 510. System 510 includes catheter shaft 512. Electrode assembly 530 may be assembled onto distal ablation tip 524 in a manner similar to what is disclosed herein. For example, electrode assembly 530 may be disposed about distal ablation tip 524. Mechanical interconnecting members 538 may extend through openings in distal ablation tip 524 to secure electrode assembly 530 to system 510 (and/or distal ablation tip 524). In at least some instances, distal ablation tip 524 takes the form of a distal ablation tip electrode 524.

Figure 15:
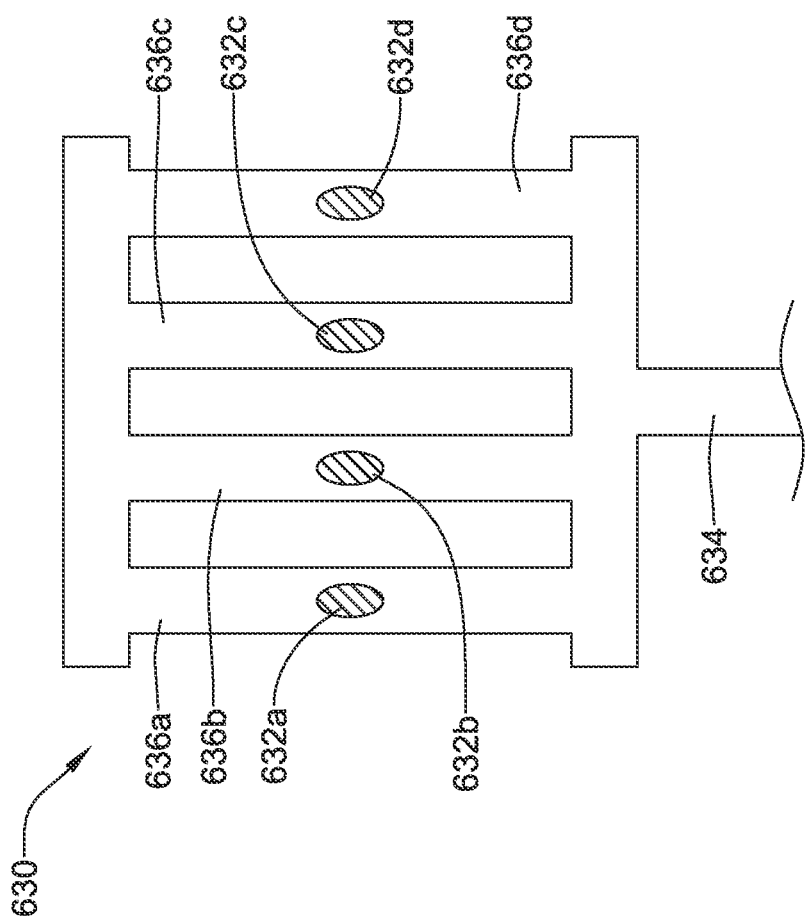
FIG. 15 is a side view of an example electrode assembly.

FIG. 15 illustrates another example electrode assembly 630 that may be similar in form and function to other assemblies disclosed herein and may be used, as appropriate, with the systems disclosed herein. Assembly 630 may include arms 636a/636b/636c/636d and proximal connector 634. Each of arms 636a/636b/636c/636d may include one or more electrodes such as electrodes 632a/632b/632c/632d. Assembly 630 may be rolled into a cylindrical configuration as shown in FIG. 16.

Figure 17:
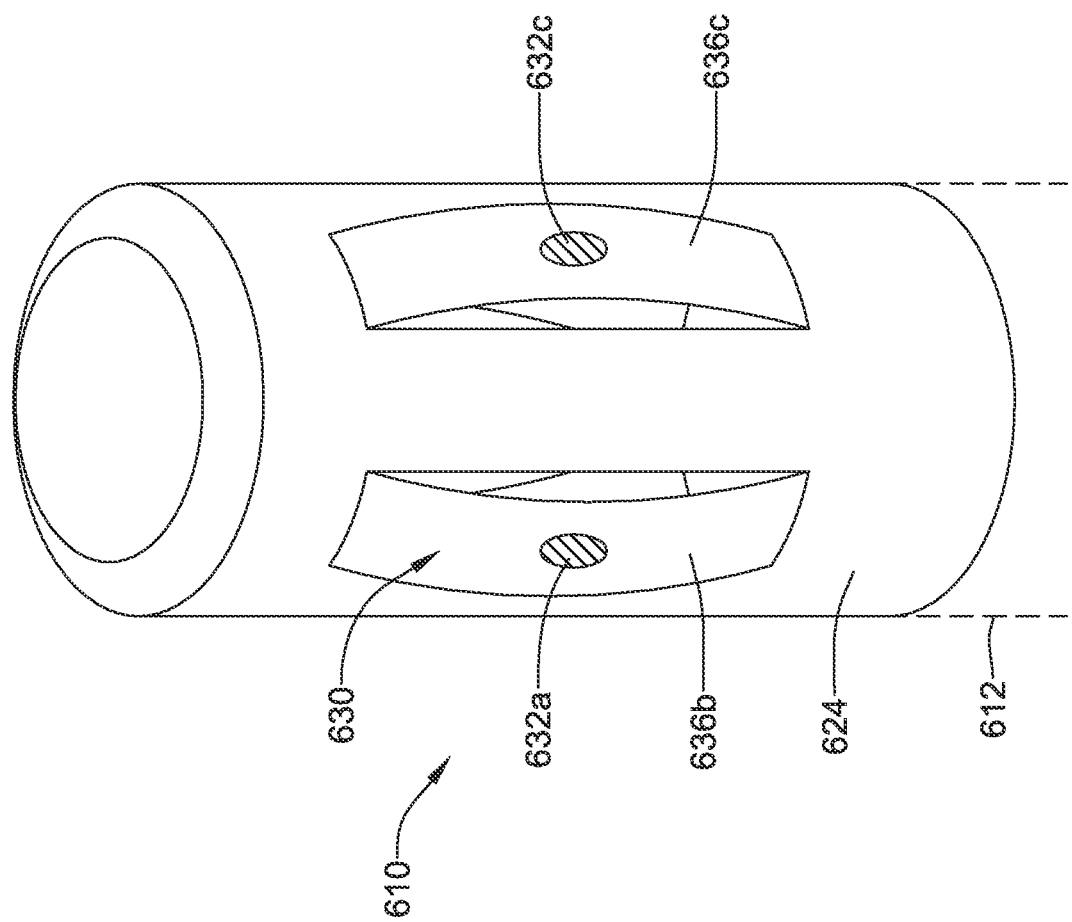
FIG. 17 is a side view of a portion of an example cardiac mapping and/or ablation system.

FIG. 17 illustrates system 610. System 610 includes catheter shaft 612. Electrode assembly 630 may be assembled along distal ablation tip 624 in a manner similar to what is disclosed herein. For example, electrode assembly 630 may be disposed within distal ablation tip 624. When assembled, arms 636a/636b/636c/636d extend through openings in distal ablation tip 624 and bow radially outward. This may be due to the application of a compressive force on electrode assembly 630 during the assembly process. Alternatively, an elastomeric gasket may be disposed within electrode assembly 630 in order to bias arms 636a/636b/636c/636d radially outward and/or seal the openings along distal ablation tip 624. The use of a gasket may allow the openings in distal ablation tip 624 to be sealed without the use of an adhesive. In addition, the use of a gasket may also allow for additional structures to be disposed along the interior of distal ablation tip 624. In some instances, the proximal and/or distal ends of assembly 630 may be secured to the inner surface of distal ablation tip 624. Although not expressly shown, system 610 may include one or more irrigation ports, for example along distal ablation tip 624. In at least some instances, distal ablation tip 624 takes the form of a distal ablation tip electrode 624.

The use of electrode assembly 630 may desirable for a number of reasons. For example, using electrode assembly 630 may allow for assembly of system 610 while reducing/ minimizing the possibility of damaging iridium oxide sputtered electrodes and/or to the parylene coating (e.g., when electrode assembly 630 includes such structures). The length of electrode assembly 630 exposed along the outer surface of system 610 may also be reduced, which may reduce the likelihood of electrode assembly 630 catching during a procedure and also may reduce the amount of surface area along distal ablation tip 624 that may be covered.

Figure 16:
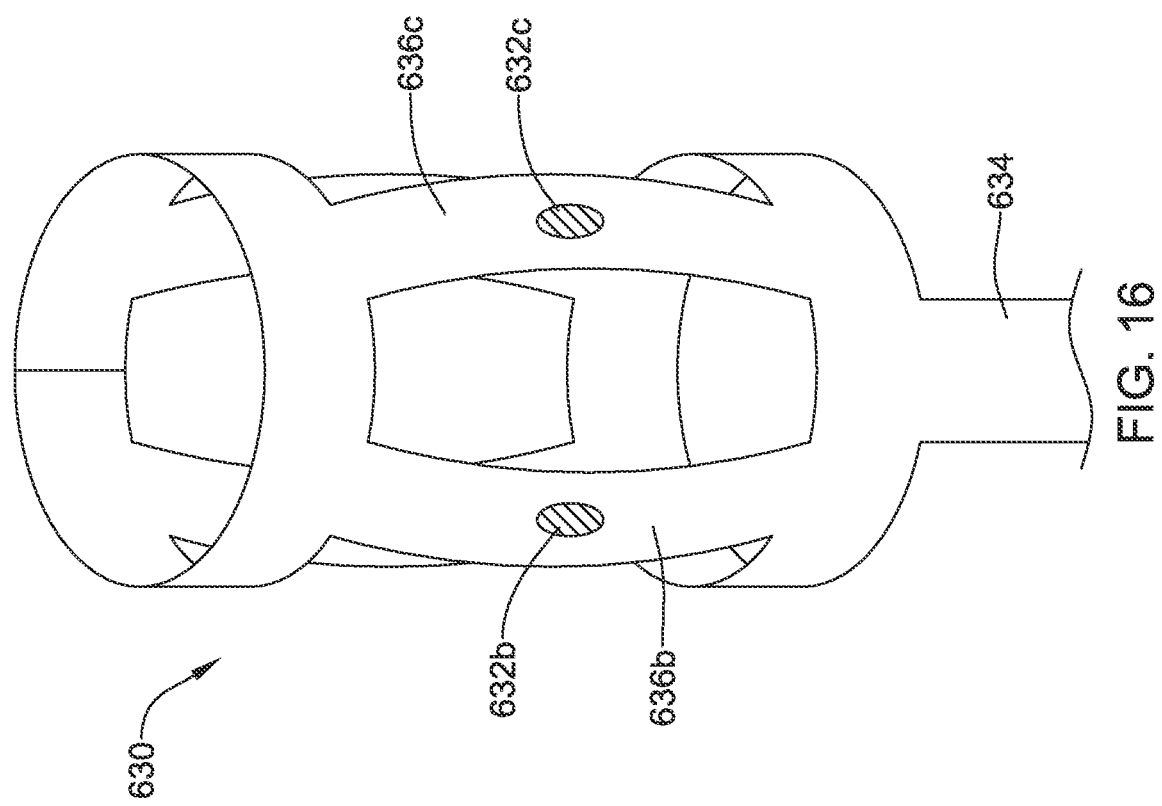
FIG. 16 is a perspective view of an example electrode assembly in a cylindrical configuration.

While FIGS. 14-16 illustrate arms 636a/636b/636c/636d oriented in an axial direction, electrode assembly 630 may also be arranged so that arms 636a/636b/636c/636d extend circumferentially or otherwise in a direction that is substantially transverse to the longitudinal axis of electrode assembly 630.

Figure 18:
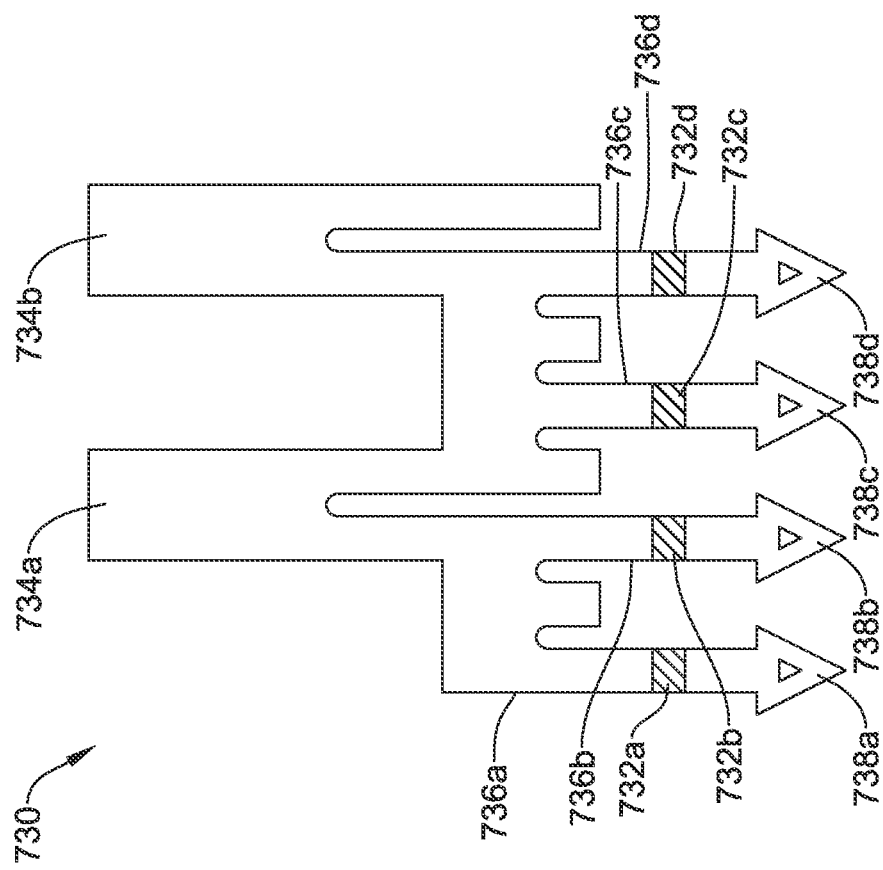
FIG. 18 is a side view of an example electrode assembly.
Figure 19:
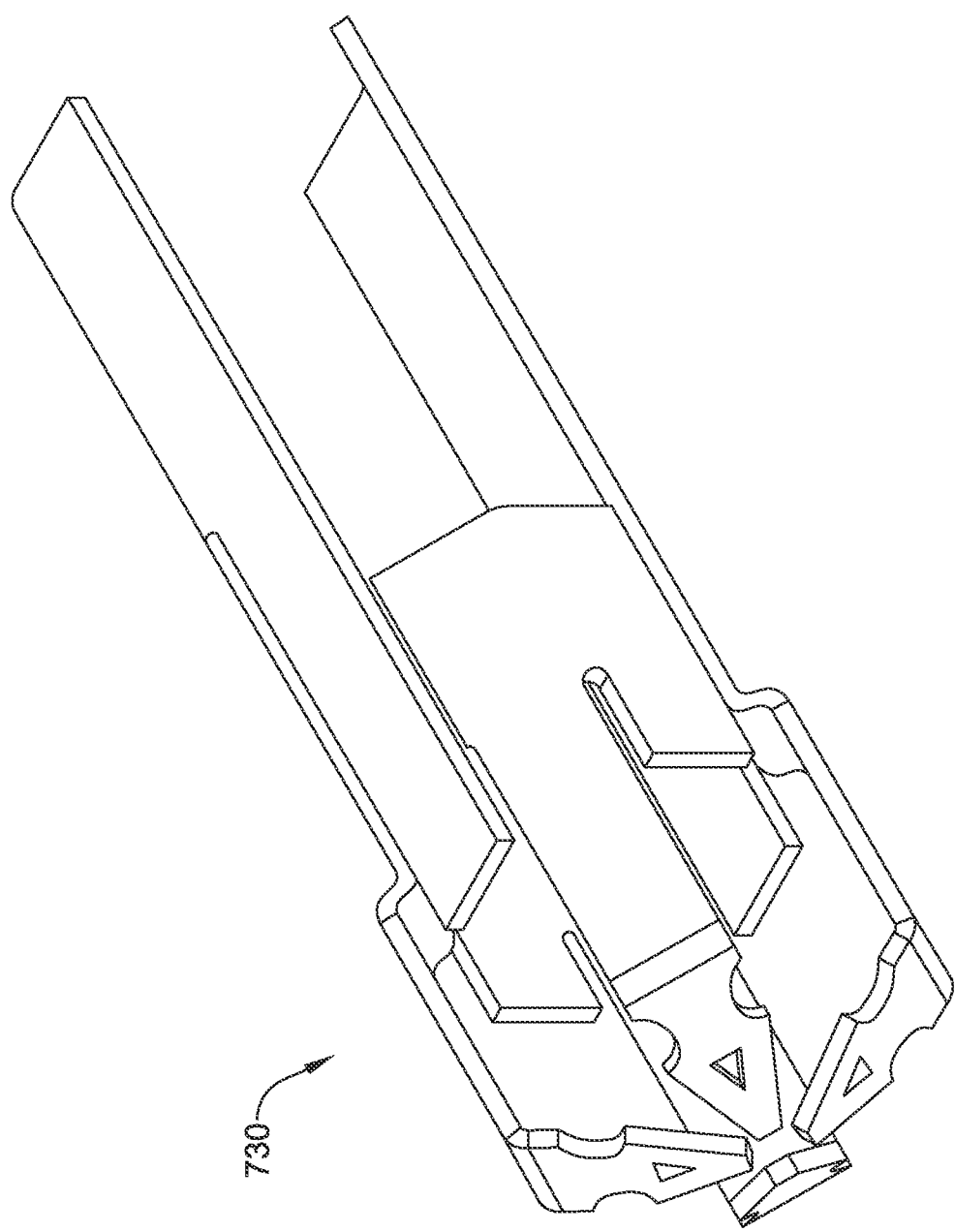
FIG. 19 is a perspective view of an example electrode assembly in a cylindrical configuration.

FIG. 18 illustrates another example electrode assembly 730 that may be similar in form and function to other assemblies disclosed herein and may be used, as appropriate, with the systems disclosed herein. Assembly 730 may include arms 736a/736b/736c/736d. Each of arms 736a/736b/736c/736d may include one or more electrodes such as electrodes 732a/732b/732c/732d and mechanical interconnecting members 738a/738b/738c/738d. Assembly 730 may also include a pair of proximal connectors 734a/734b. Assembly 730 may be formed into a generally cylindrical configuration as shown in FIG. 19.

Figure 20:
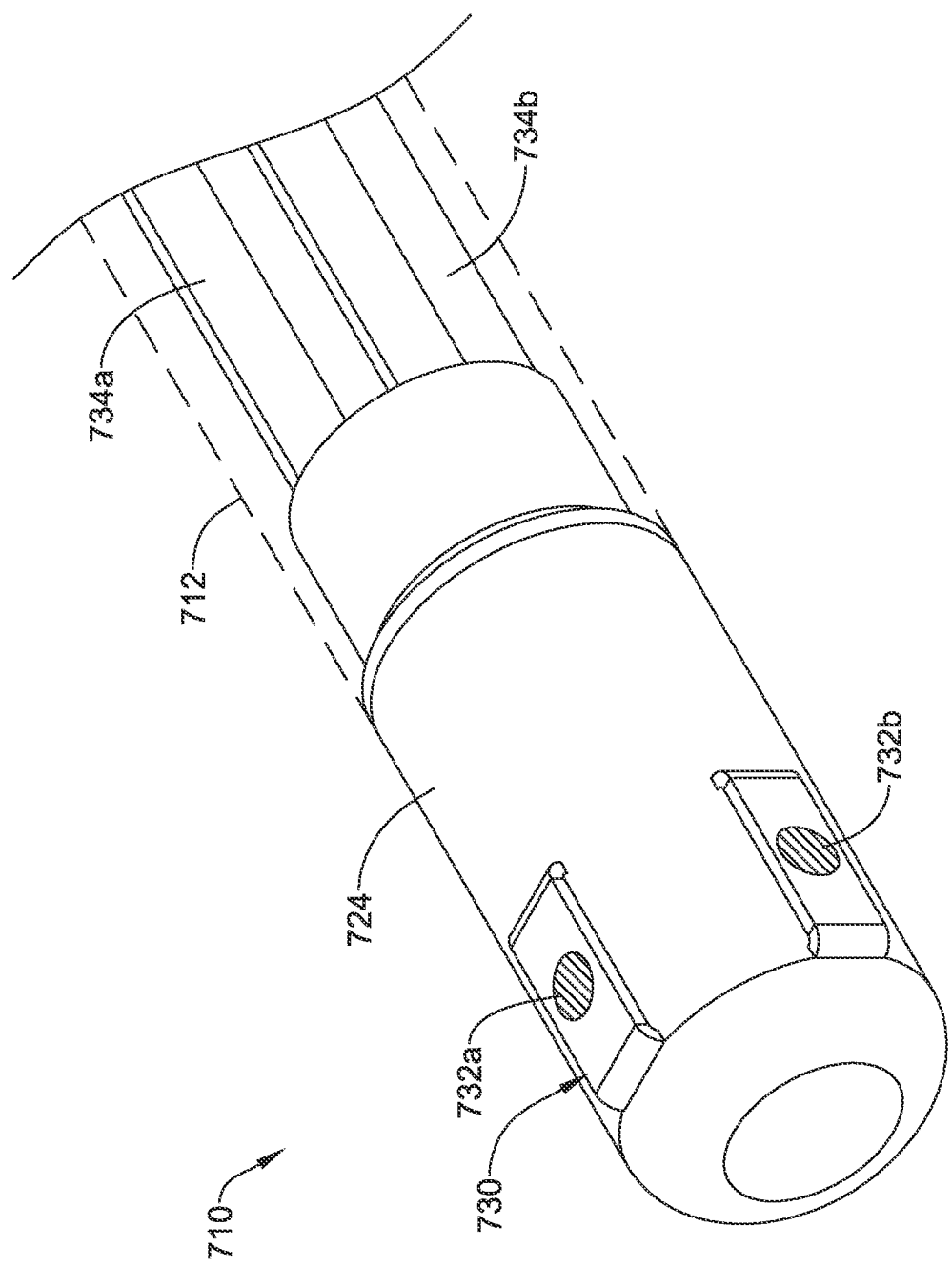
FIG. 20 is a side view of a portion of an example cardiac mapping and/or ablation system.

FIG. 20 illustrates system 710. System 710 includes catheter shaft 712. Electrode assembly 730 may be assembled along distal ablation tip 724 in a manner similar to what is disclosed herein. For example, mechanical interconnecting members 738a/738b/738c/738d may extend through openings in distal ablation tip 724 to secure assembly 730 to system 710 (and/or to distal ablation tip 724). In at least some instances, distal ablation tip 724 takes the form of a distal ablation tip electrode 724.

Figure 21:
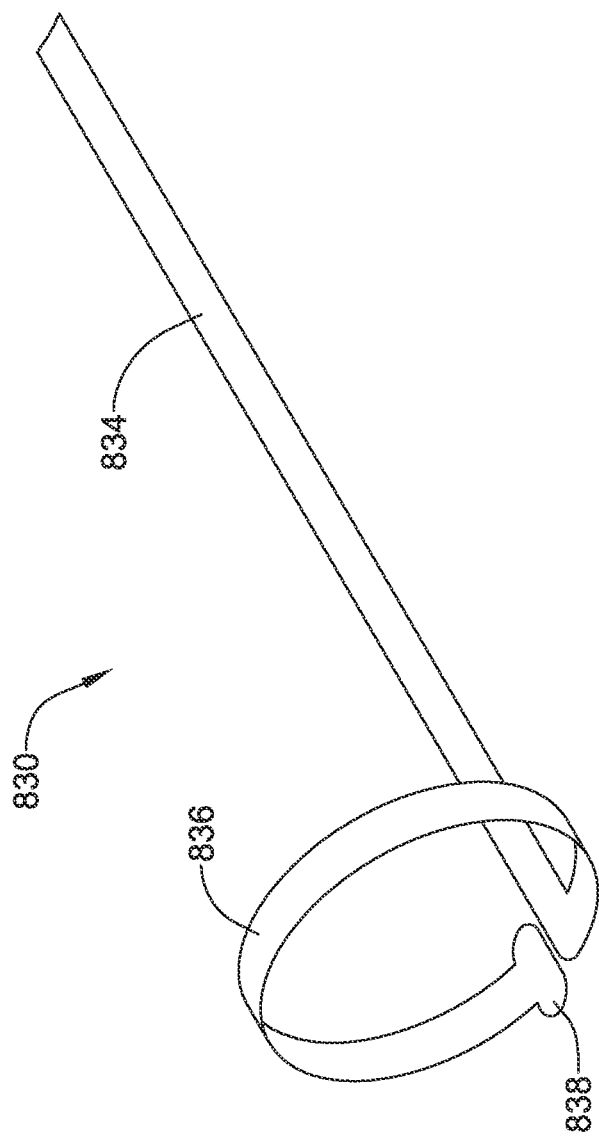
FIG. 21 is a perspective view of an example electrode assembly.
Figure 22:
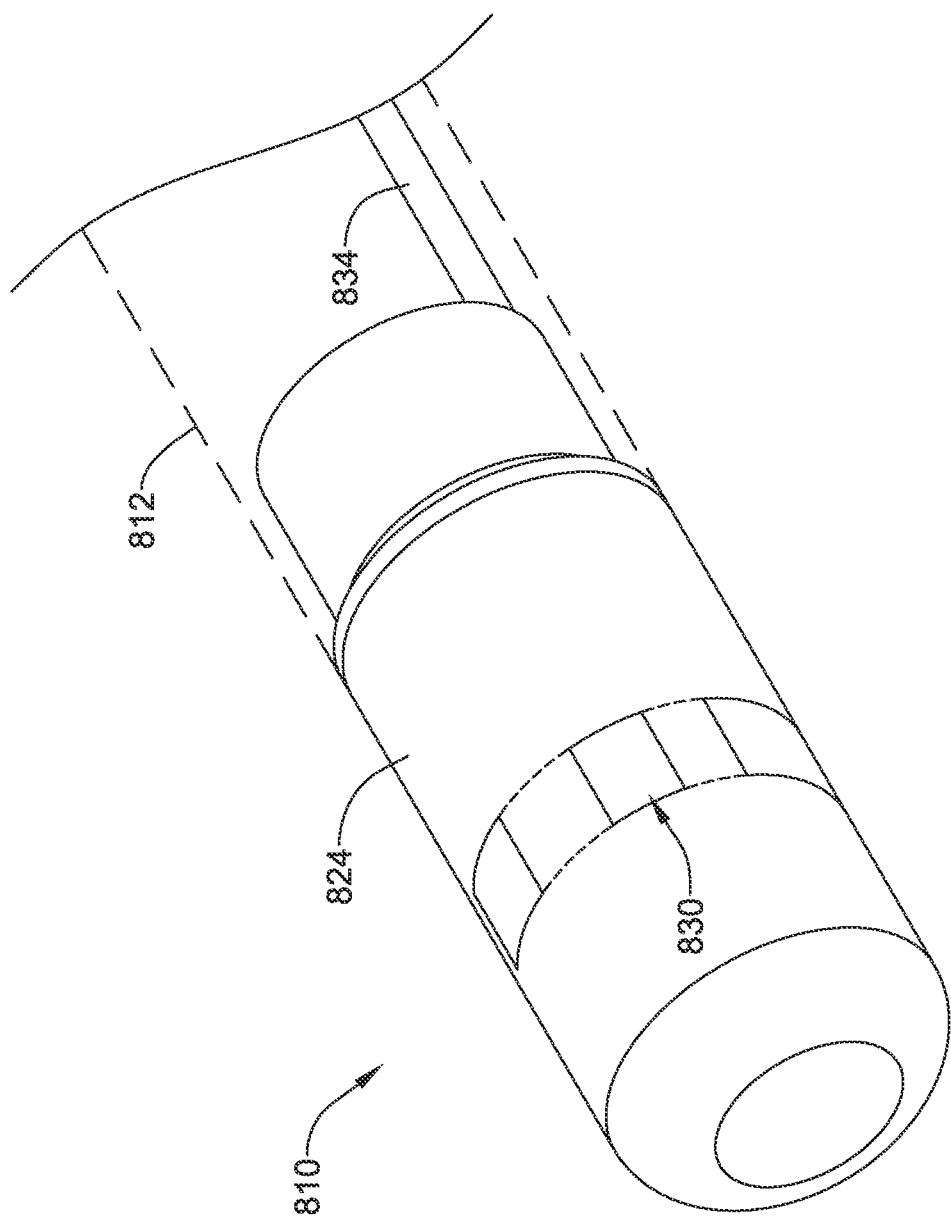
FIG. 22 is a partially cutaway perspective view of a portion of an example cardiac mapping and/or ablation system.

FIG. 21 illustrates another example electrode assembly 830 that may be similar in form and function to other assemblies disclosed herein and may be used, as appropriate, with the systems disclosed herein. Assembly 830 may include arm 836, mechanical interconnecting member 838, and proximal connector 834. FIG. 22 illustrates system 810. System 810 includes catheter shaft 812. Electrode assembly 830 may be assembled along distal ablation tip 824 in a manner similar to what is disclosed herein. For example, electrode assembly 830 may be wrapped circumferentially about distal ablation tip 824. Alternatively, electrode assembly 830 may be woven in and out of openings formed in distal ablation tip 824. In at least some instances, distal ablation tip 824 takes the form of a distal ablation tip electrode 824.

Figure 23:
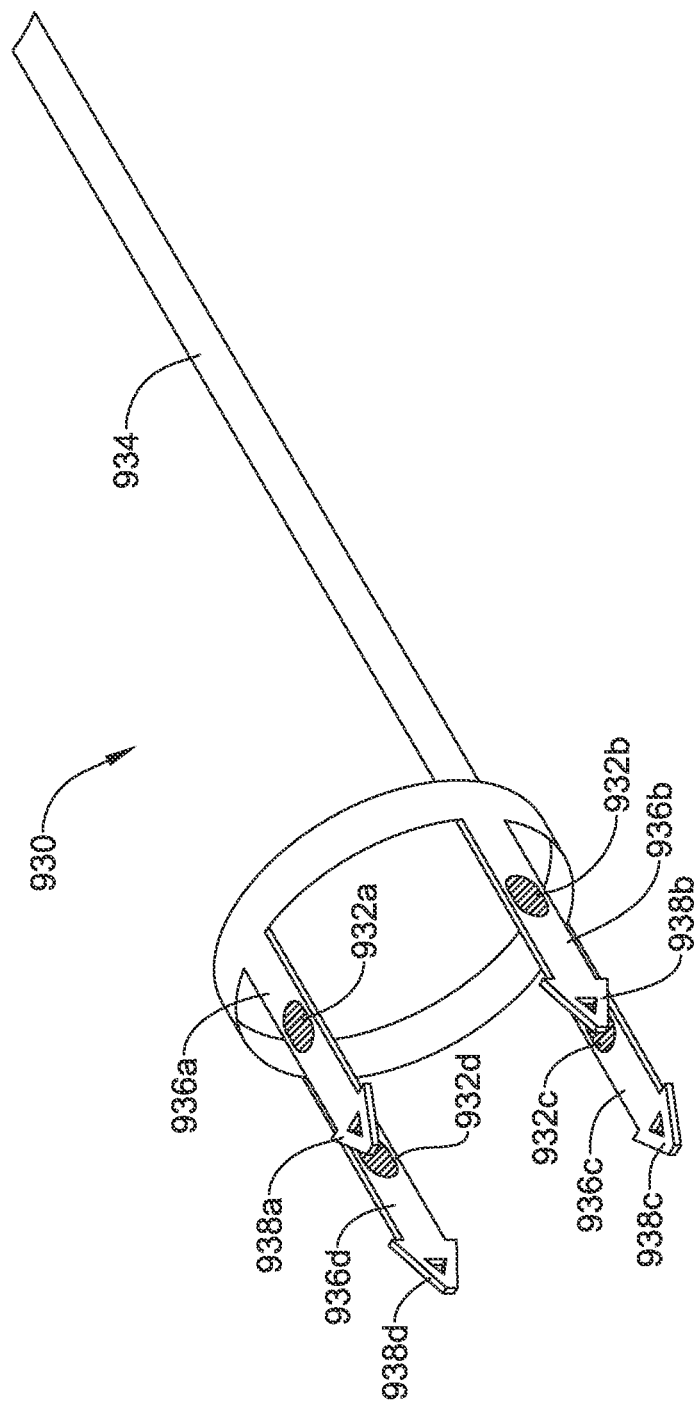
FIG. 23 is a perspective view of an example electrode assembly.

FIG. 23 illustrates another example electrode assembly 930 that may be similar in form and function to other assemblies disclosed herein and may be used, as appropriate, with the systems disclosed herein. Assembly 930 may include arms 936a/936b/936c/936d. Each of arms 936a/936b/936c/936d may include one or more electrodes such as electrodes 932a/932b/932c/932d and mechanical interconnecting members 938a/938b/938c/938d. Assembly 930 may also include proximal connector 934.

Figure 24:
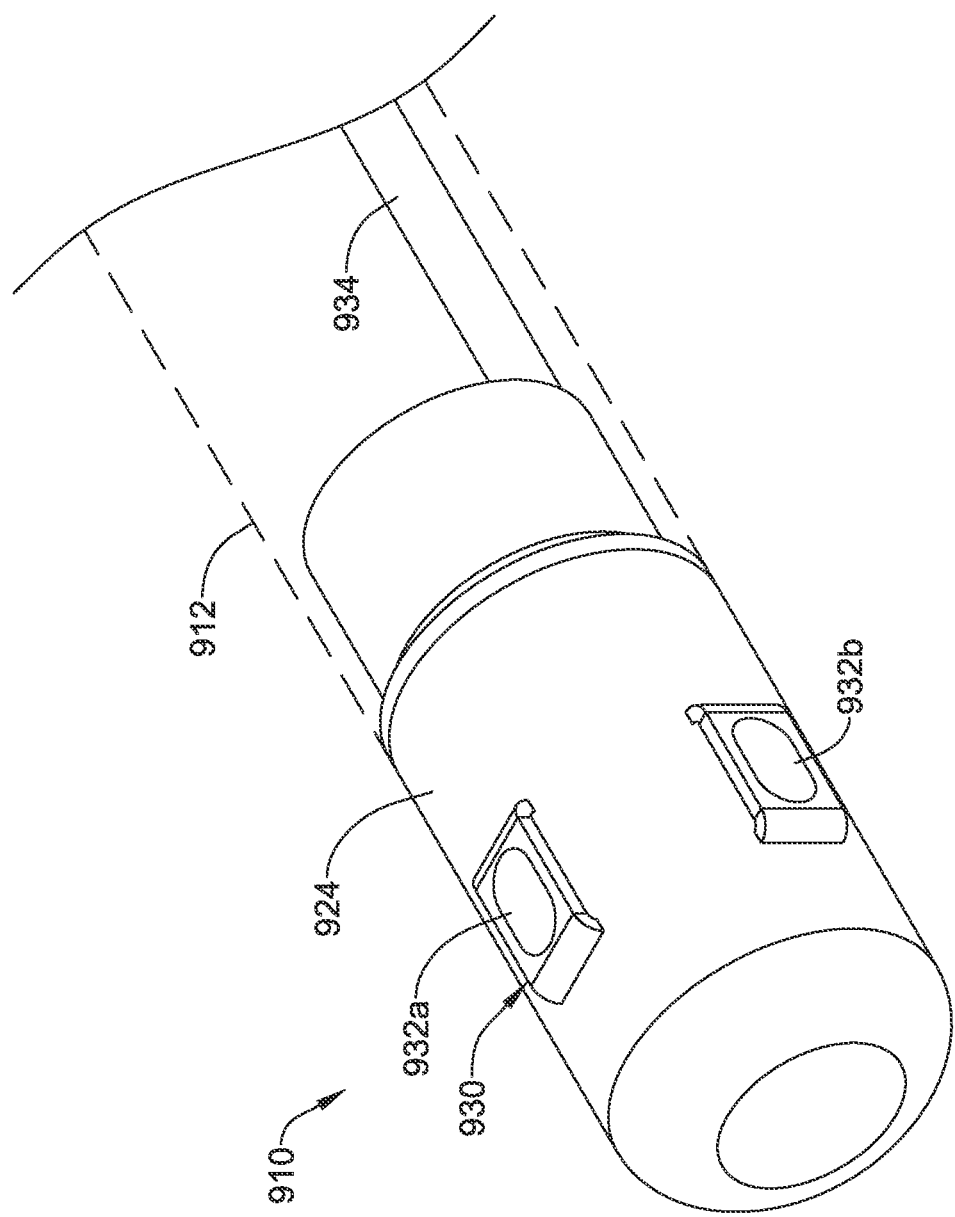
FIG. 24 is a partially cutaway perspective view of a portion of an example cardiac mapping and/or ablation system.

FIG. 24 illustrates system 910. System 910 includes catheter shaft 912. Electrode assembly 930 may be assembled along distal ablation tip 924 in a manner similar to what is disclosed herein. For example, mechanical interconnecting members 938a/938b/938c/938d may extend through openings in distal ablation tip 924 to secure assembly 930 to system 910 (and/or to distal ablation tip 924). In at least some instances, distal ablation tip 924 takes the form of a distal ablation tip electrode 924.

Figure 25:
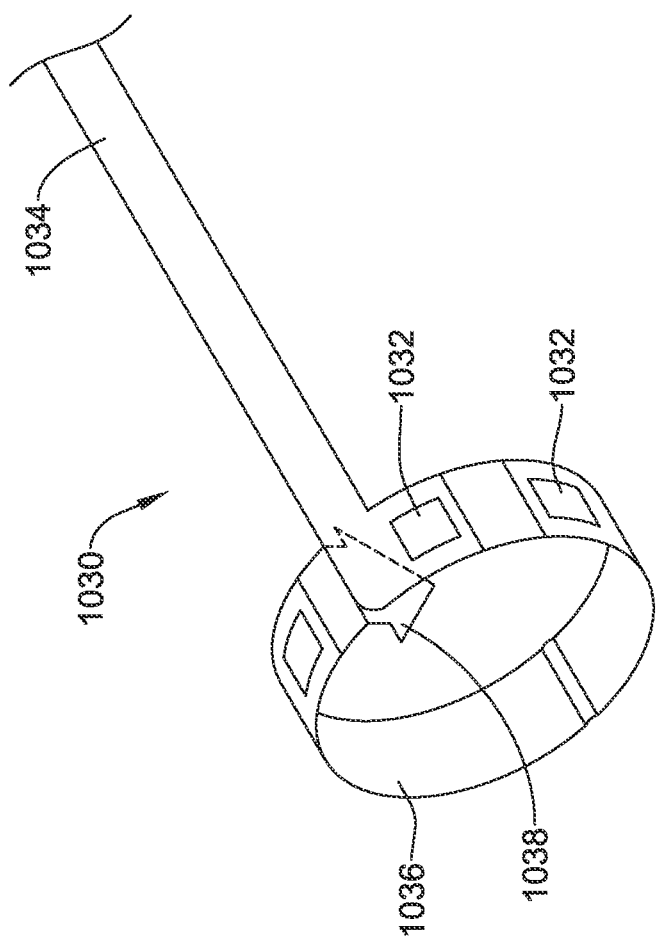
FIG. 25 is a perspective view of an example electrode assembly.

FIG. 25 illustrates another example electrode assembly 1030 that may be similar in form and function to other assemblies disclosed herein and may be used, as appropriate, with the systems disclosed herein. Assembly 1030 may include arm 1036 arranged in a cylindrical orientation. A plurality of electrodes 1032 may be disposed along arm 1036. Mechanical interconnecting member 1038 may be disposed on an end region of arm 1036. Assembly 1030 may also include proximal connector 1034.

Figure 26:
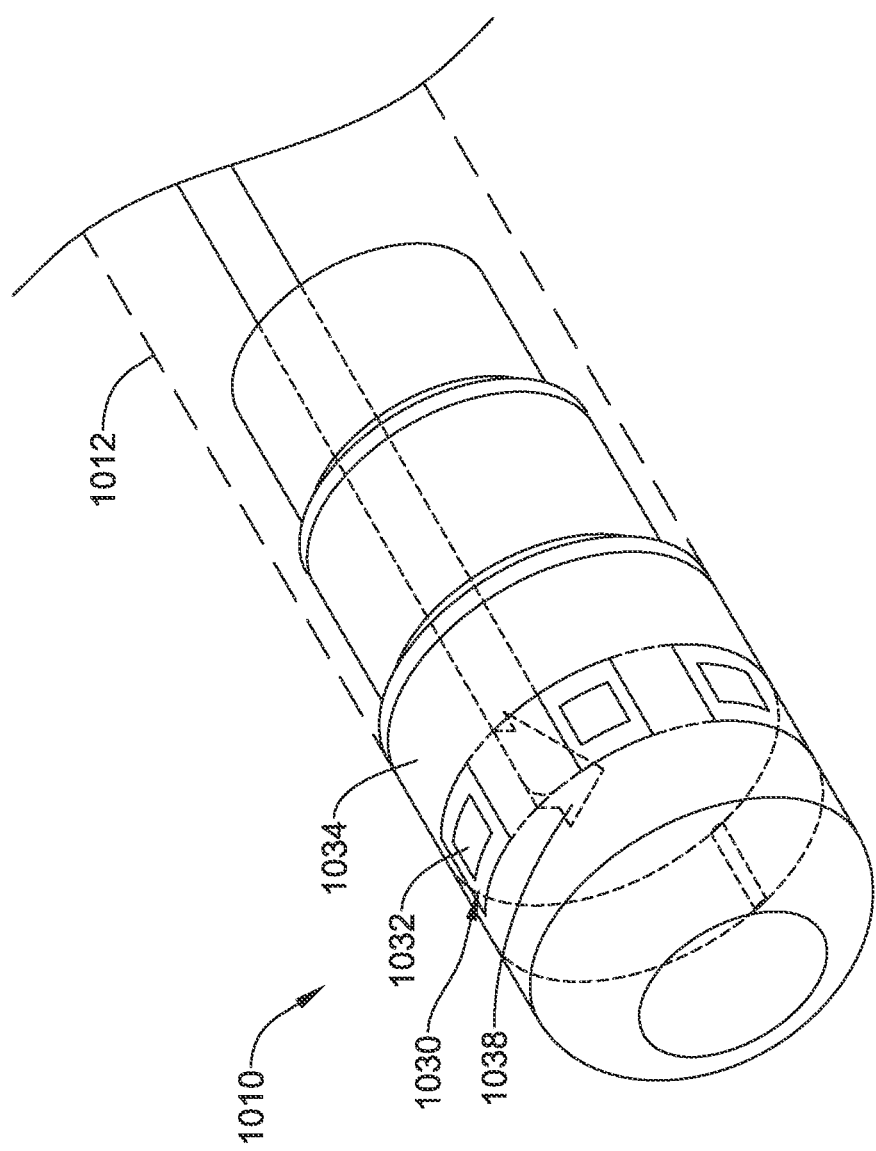
FIG. 26 is a partially cutaway perspective view of a portion of an example cardiac mapping and/or ablation system.

FIG. 26 illustrates system 1010. System 1010 includes catheter shaft 1012. Electrode assembly 1030 may be assembled along distal ablation tip 1024 in a manner similar to what is disclosed herein. For example, mechanical interconnecting member 1038 may extend through openings in distal ablation tip 1024 to secure assembly 1030 to system 1010 (and/or to distal ablation tip 1024). In at least some instances, distal ablation tip 1024 takes the form of a distal ablation tip electrode 1024.

Figure 27:
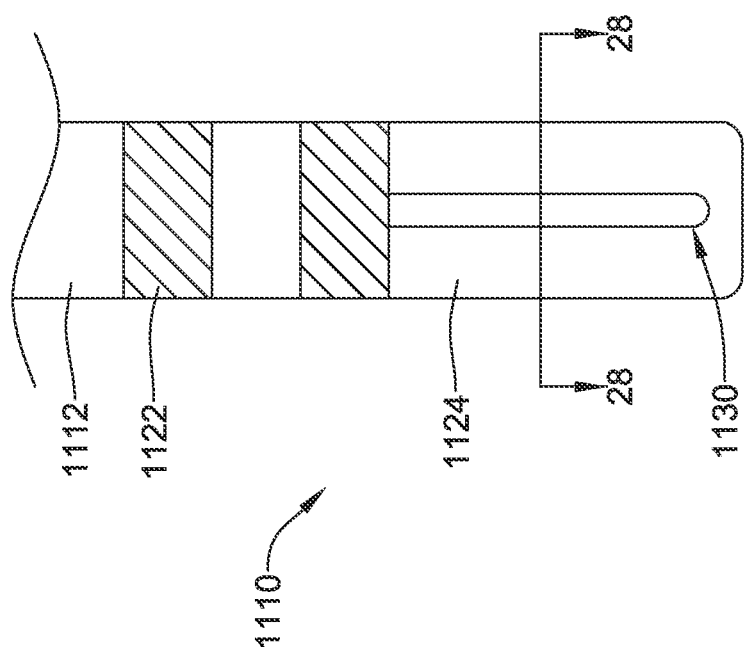
FIG. 27 is a side view of a portion of an example cardiac mapping and/or ablation system.

FIG. 27 is a side view of another example system 1110 that may be similar in form and function to other systems disclosed herein. System 1110 includes shaft 1112. One or more ring electrodes 1122 may be disposed along shaft 1112. Distal ablation tip 1124 may be disposed at the distal end of shaft 1112. Electrode assembly 1130 may be disposed along distal ablation tip 1124. For example, electrode assembly 1130 may be attached to distal ablation tip 1124 using an adhesive or other suitable attachment mechanism. In some embodiments, a single electrode assembly 1130 may be disposed along distal ablation tip 1124. In other embodiments, a plurality of electrode assemblies 1130 (e.g., 2-8 or more) may be disposed along distal ablation tip 1124. In at least some instances, distal ablation tip 1124 takes the form of a distal ablation tip electrode 1124. Each electrode assembly 1130 may be formed from a dielectric material disposed along distal ablation tip 1124 with a strip of electrode material (e.g., 300 series stainless steel, gold, platinum, copper, etc.) disposed along the dielectric material. Electrode assembly 1130 may have a width of about 0.01-0.04 inches (e.g., about 0.025 inches) and a length of about 1-5 millimeters (e.g., 3 mm or about 0.118 inches). These are just examples.

Figure 28:
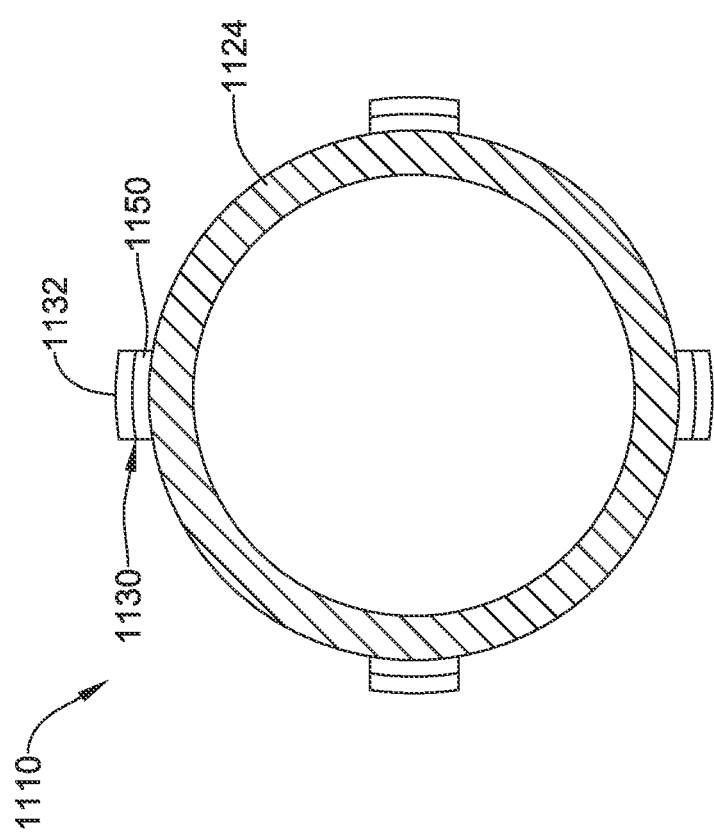
FIG. 28 is a cross-sectional view taken through line 28-28.

FIG. 28 is a cross-sectional view of a portion of system 1110. Here it can be seen that electrode assembly 1130 may include an inner insulating layer 1150 and an outer conductive layer or electrode regions 1132. In some of these and in other embodiments, electrode assembly 1130 may include a flexible circuit as disclosed herein.

Figure 29:
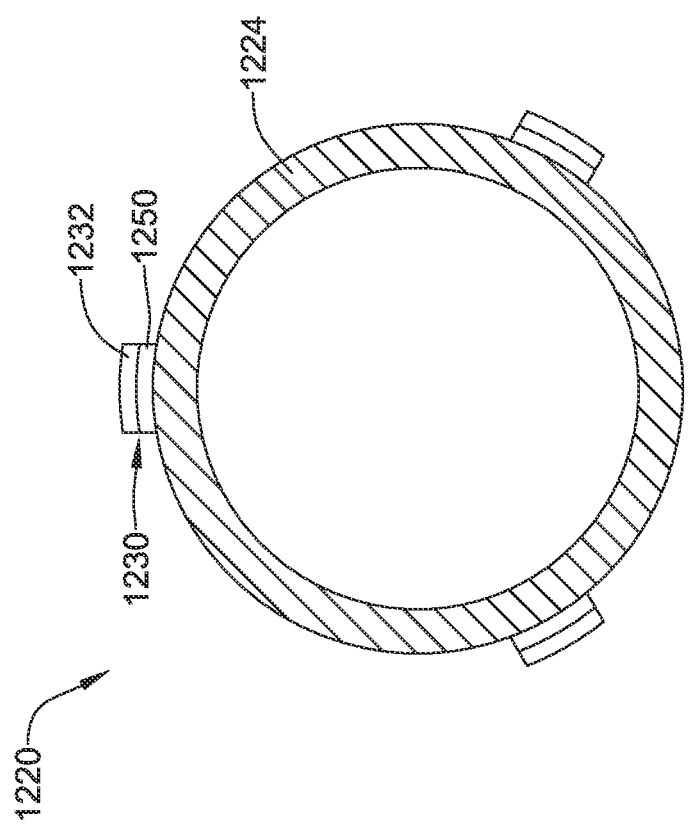
FIG. 29 is an alternative cross-sectional view taken through line 28-28.

While FIG. 28 shows that four electrode assemblies 1130 may be disposed about system 1110, this is not intended to be limiting. For example, FIG. 29 illustrates system 1220 that includes three electrode assemblies 1230 are disposed along distal ablation tip 1224. In at least some instances, distal ablation tip 1224 takes the form of a distal ablation tip electrode 1224. Similarly to electrode assemblies 1130, electrode assemblies 1230 may include inner insulating layer 1250 and outer conductive layer or electrode region 1232.

Figure 30:
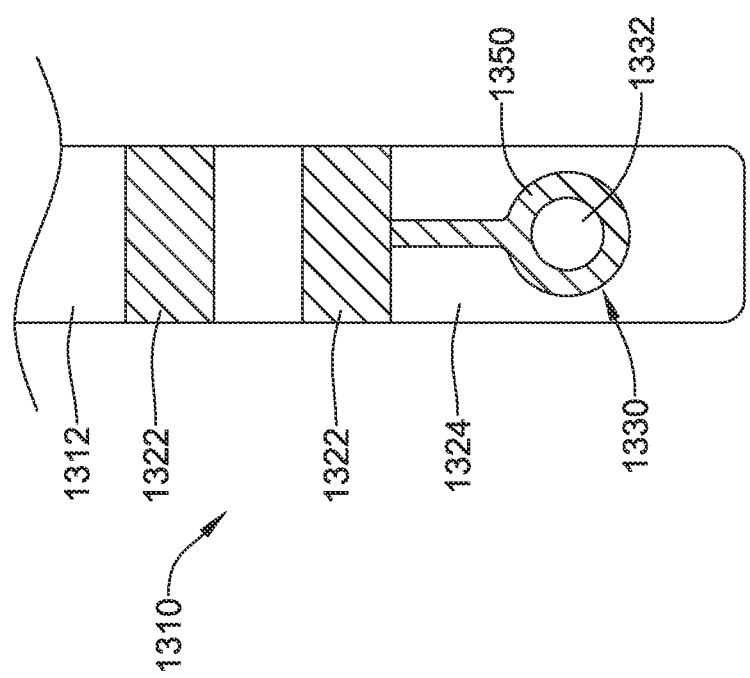
FIG. 30 is a side view of a portion of an example cardiac mapping and/or ablation system.

FIG. 30 is a side view of another example system 1310 that may be similar in form and function to other systems disclosed herein. System 1310 includes shaft 1312. One or more ring electrodes 1322 may be disposed along shaft 1312. Distal ablation tip 1324 may be disposed at the distal end of shaft 1312. Electrode assembly 1330 may be disposed along distal ablation tip 1324. Electrode assembly 1330 may include insulating layer 1350 and electrode region 1332. In this example, electrode region 1332 may take the form of a discrete electrode surrounded by insulating layer 1350. In at least some instances, distal ablation tip 1324 takes the form of a distal ablation tip electrode 1324.

Figure 31:
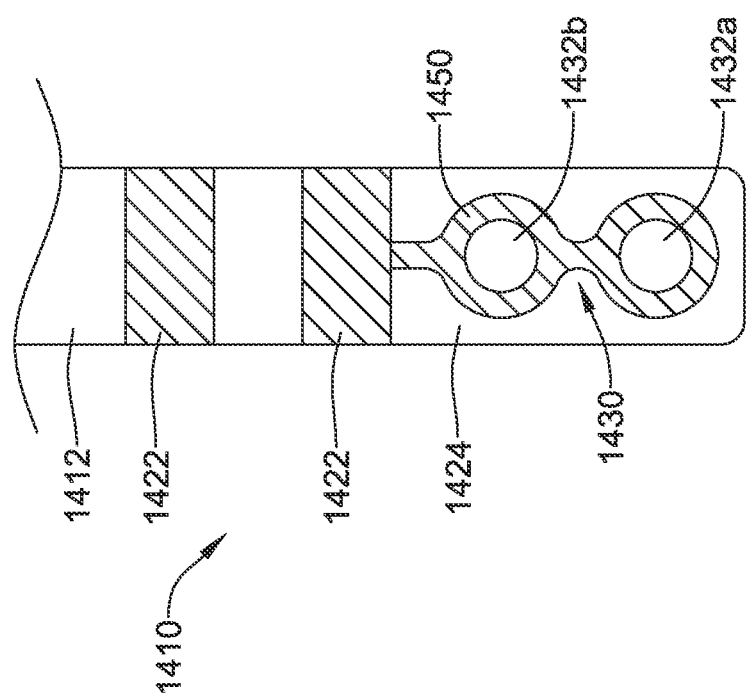
FIG. 31 is a side view of a portion of an example cardiac mapping and/or ablation system.

FIG. 31 is a side view of another example system 1410 that may be similar in form and function to other systems disclosed herein. System 1410 includes shaft 1412. One or more ring electrodes 1422 may be disposed along shaft 1412. Distal ablation tip 1424 may be disposed at the distal end of shaft 1412. Electrode assembly 1430 may be disposed along distal ablation tip 1424. Electrode assembly 1430 may include insulating layer 1450 and a plurality of electrode regions 1432a/1432b. In at least some embodiments, electrode regions 1432a/1432b may be a pair of bipolar electrodes. In at least some instances, distal ablation tip 1424 takes the form of a distal ablation tip electrode 1424.

Figure 32:
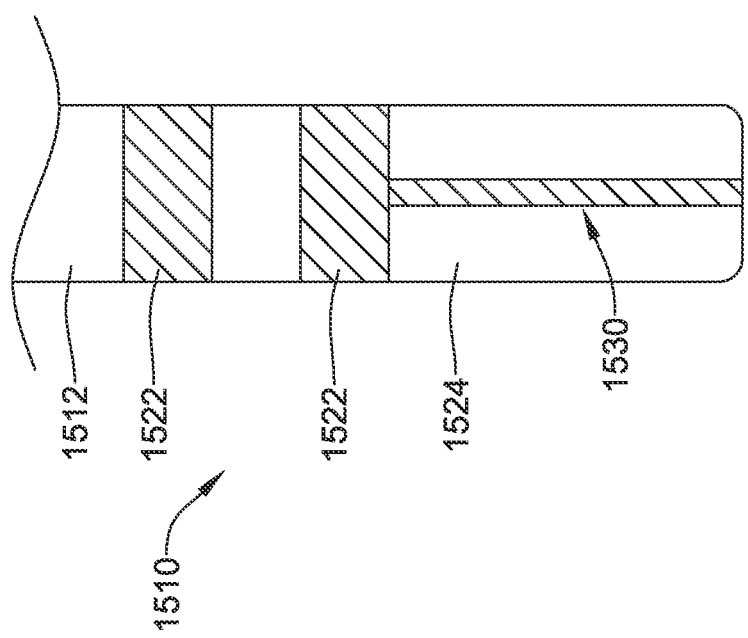
FIG. 32 is a side view of a portion of an example cardiac mapping and/or ablation system.
Figure 33:
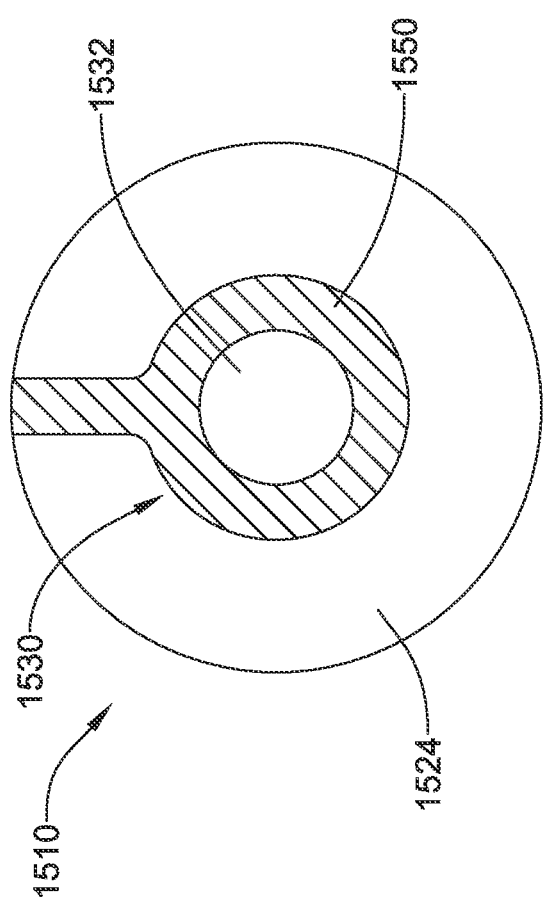
FIG. 33 is an end view of the example cardiac mapping and/or ablation system shown in FIG. 32.

FIGS. 32-33 illustrate another example system 1510 that may be similar in form and function to other systems disclosed herein. System 1510 includes shaft 1512. One or more ring electrodes 1522 may be disposed along shaft 1512. Distal ablation tip 1524 may be disposed at the distal end of shaft 1512. In at least some instances, distal ablation tip 1524 takes the form of a distal ablation tip electrode 1524.

Electrode assembly 1530 may be disposed along distal ablation tip 1524. In this example, electrode assembly 1530 may extend to and/or along the distal end of distal ablation tip 1524 as can be seen in FIG. 33, which is an end view of system 1510. Here it can be seen that electrode assembly 1530 may include insulating layer 1550 and electrode region 1532.

Figure 34:
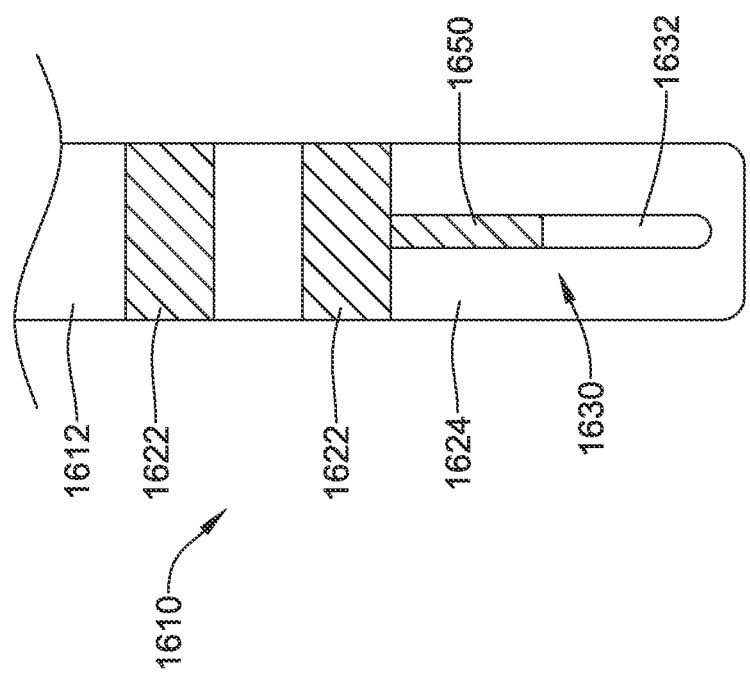
FIG. 34 is a side view of a portion of an example cardiac mapping and/or ablation system.

FIG. 34 is a side view of another example system 1610 that may be similar in form and function to other systems disclosed herein. System 1610 includes shaft 1612. One or more ring electrodes 1622 may be disposed along shaft 1612. Distal ablation tip 1624 may be disposed at the distal end of shaft 1612. In at least some instances, distal ablation tip 1624 takes the form of a distal ablation tip electrode 1624.

Electrode assembly 1630 may be disposed along distal ablation tip 1624. Electrode assembly 1630 may include insulating layer 1650 and electrode region 1632.

Figure 35:
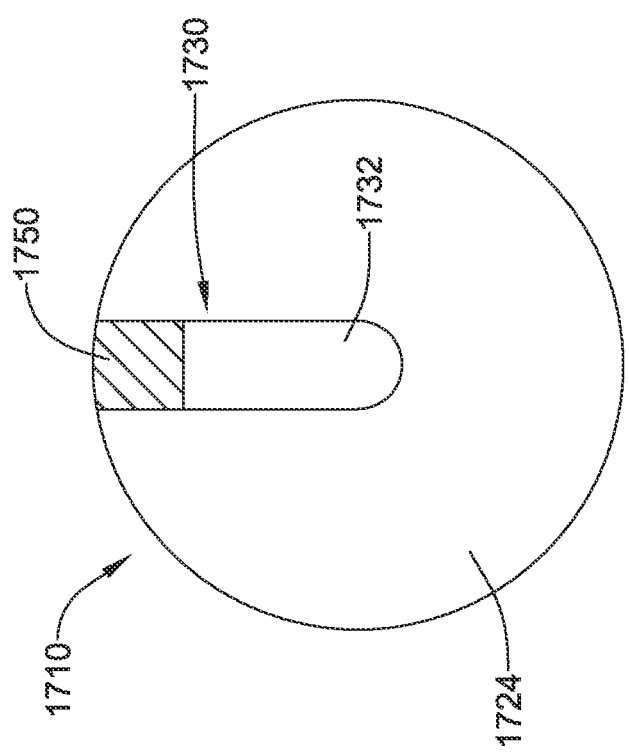
FIG. 35 is an end view of an example cardiac mapping and/or ablation system shown.

FIG. 35 is an end view of another example system 1710 that may be similar in form and function to other systems disclosed herein. System 1710 includes distal ablation tip 1724. Electrode assembly 1730 may be disposed along distal ablation tip 1724. Electrode assembly 1730 may include insulating layer 1750 and electrode region 1732. In at least some instances, distal ablation tip 1724 takes the form of a distal ablation tip electrode 1724.

Figure 36:
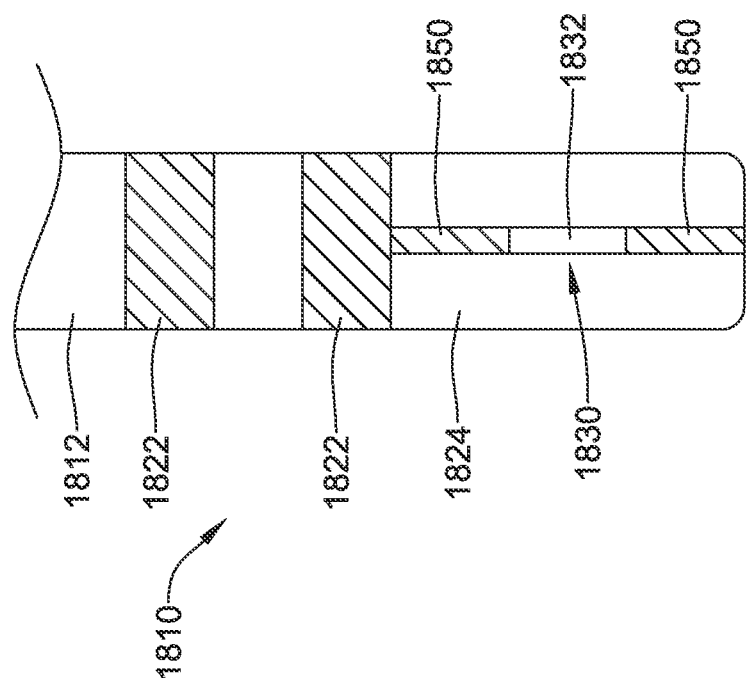
FIG. 36 is a side view of a portion of an example cardiac mapping and/or ablation system.

FIG. 36 is a side view of another example system 1810 that may be similar in form and function to other systems disclosed herein. System 1810 includes shaft 1812. One or more ring electrodes 1822 may be disposed along shaft 1812. Distal ablation tip 1824 may be disposed at the distal end of shaft 1812. In at least some instances, distal ablation tip 1824 takes the form of a distal ablation tip electrode 1824.

Electrode assembly 1830 may be disposed along distal ablation tip 1824. Electrode assembly 1830 may include a plurality of insulating layers 1850 and electrode region 1832 disposed between insulating layers 1850.

Figure 37:
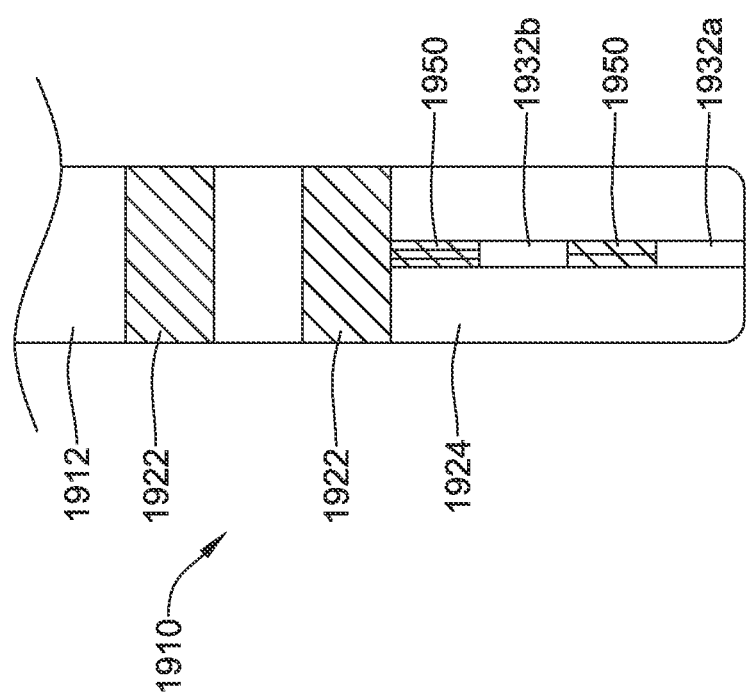
FIG. 37 is a side view of a portion of an example cardiac mapping and/or ablation system.

FIG. 37 is a side view of another example system 1910 that may be similar in form and function to other systems disclosed herein. System 1910 includes shaft 1912. One or more ring electrodes 1922 may be disposed along shaft 1912. Distal ablation tip 1924 may be disposed at the distal end of shaft 1912. In at least some instances, distal ablation tip 1924 takes the form of a distal ablation tip electrode 1924.

Electrode assembly 1930 may be disposed along distal ablation tip 1924. Electrode assembly 1930 may include a plurality of insulating layers 1950 and a plurality of electrode regions 1932a/1932b disposed between insulating layers 1950.

The materials that can be used for the various components of system 10 and/or other systems disclosed herein (e.g., shafts, micro-electrodes, distal ablation tip electrodes, flexible circuits, substrates, etc.) may include metals, metal alloys, polymers, metal-polymer composites, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, components of system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of system 10 to achieve the same result.

In some embodiments, a degree of Magnetic Resonance Imaging (MRI) compatibility is imparted into system 10. For example, components of system 10, or portions thereof, may be made of a material that does not substantially distort the image and create substantial artifacts (e.g., gaps in the image). Certain ferromagnetic materials, for example, may not be suitable because they may create artifacts in an MRI image. Components of system 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A catheter for use in cardiac mapping and/or ablation, the catheter comprising:

an elongate catheter shaft having a distal ablation electrode configured to contact and provide ablation energy to tissue, wherein the distal ablation electrode comprises a plurality of openings extending through an exterior surface of the distal ablation tip;

an electrode assembly releasably coupled to the distal ablation electrode, wherein the electrode assembly comprises a plurality of members, wherein each member of the plurality of members passes through a respective opening of the plurality of openings to fix the electrode assembly relative to the distal ablation electrode when the electrode assembly is coupled to the distal ablation electrode; and wherein the electrode assembly includes a flexible circuit having one or more electrodes disposed thereon.

2. The catheter of claim 1, wherein the electrode assembly includes a region that is disposed along a distal end of the distal ablation electrode.

3. The catheter of claim 1, wherein the plurality of members comprises wherein each member of the plurality of members includes at least one electrode.

4. The catheter of claim 3, wherein the electrode assembly includes three or more members.

5. The catheter of claim 3, wherein the electrode assembly includes four or more members.

6. The catheter of claim 1, wherein each member has an arrow shape.

7. The catheter of claim 1, wherein each member has relief cutouts.

8. The catheter of claim 1, wherein the catheter shaft includes an inner channel, wherein the distal ablation electrode region includes a first opening, and wherein the electrode assembly extends along the inner channel, through the first opening.

9. The catheter of claim 1, wherein the electrode assembly is adhesively bonded to the distal ablation electrode.

10. The catheter of claim 1, wherein the electrode assembly includes one or more electrode regions and one or more electrically insulated regions.

11. The catheter of claim 1, wherein the electrode assembly extends circumferentially around the distal ablation electrode.

12. The catheter of claim 1, wherein the electrode assembly is designed to bow radially outward from the distal ablation electrode.

13. The catheter of claim 1, wherein the distal ablation electrode includes a platinum ablation tip electrode.

14. The catheter of claim 1, wherein each member has a rounded shape.

15. A method for manufacturing a medical device, the method comprising:
   inserting an electrode assembly into a channel formed within a distal ablation tip of a catheter, the distal ablation tip configured to contact and provide ablation energy to tissue;
   wherein the electrode assembly includes a flexible circuit having one or more electrodes disposed thereon, wherein the electrode assembly comprises a plurality of members;
   wherein the distal ablation tip includes a first opening and a second opening extending through an exterior surface of the distal ablation tip; and
   extending electrode assembly through the first opening, along an outer surface of the distal ablation tip, and a member of the plurality of members through the second opening to couple and fix the electrode assembly relative to the distal ablation tip.

16. A catheter for use in cardiac mapping and/or ablation, the catheter comprising:
   an elongate catheter shaft having an inner channel and a distal end region;
   a distal ablation tip configured to ablate tissue disposed near the distal end region;
      an electrode assembly releasably coupled to the distal ablation tip;
   wherein the electrode assembly includes a flexible circuit having a plurality of arm regions, wherein each arm region includes one or more electrodes disposed thereon;
   wherein the distal ablation electrode region includes a first opening and a second opening extending through an exterior surface of the distal ablation tip;
   wherein the electrode assembly extends along the inner channel, through the first opening, and wherein an arm region of the plurality of arm regions extends along an outer surface of the distal ablation tip and through the second opening to mechanically secure the electrode assembly to the distal ablation tip.

17. The catheter of claim 16, wherein the electrode assembly includes a region that is disposed along a distal end of the distal ablation tip.

18. The catheter of claim 16, wherein each arm region has an arrow shape.

19. The catheter of claim 16, wherein each arm region has relief cutouts.

20. The catheter of claim 16, wherein each member has a rounded shape.

* * * * *